US005550131A

United States Patent [19]

Sugihara et al.

[11] Patent Number: 5,550,131

[45] Date of Patent: Aug. 27, 1996

[54] 2-PIPERAZINONE COMPOUNDS AND THEIR USE

[75] Inventors: Hirosada Sugihara, Tsukuba; Zenichi Terashita, Suita; Hideto Fukushi, Higashiosaka, all of Japan

[73] Assignee: Takeda Chemical Industries, Ltd., Osaka, Japan

[21] Appl. No.: 262,315

[22] Filed: Jun. 17, 1994

[30] Foreign Application Priority Data

| | | | |
|---|---|---|---|
| Jun. 17, 1993 | [JP] | Japan | 5-146136 |
| Oct. 12, 1993 | [JP] | Japan | 5-254142 |

[51] Int. Cl.$^6$ ...................... A61K 31/495; C07D 241/04

[52] U.S. Cl. ........................ 514/255; 544/384; 544/390

[58] Field of Search .................................. 544/384, 390; 514/255

[56] References Cited

FOREIGN PATENT DOCUMENTS

| | | |
|---|---|---|
| 0505868 | 9/1992 | European Pat. Off. . |
| 0529858 | 3/1993 | European Pat. Off. . |

OTHER PUBLICATIONS

Okamoto et al. CA 111-195407 (1988).
Okamoto et al. CA 110-108201 (1988).
Okamoto et al. CA 107-78251 (1987).

*Primary Examiner*—Cecilia Tsang
*Attorney, Agent, or Firm*—Foley & Lardner

[57] ABSTRACT

Compounds of the formula

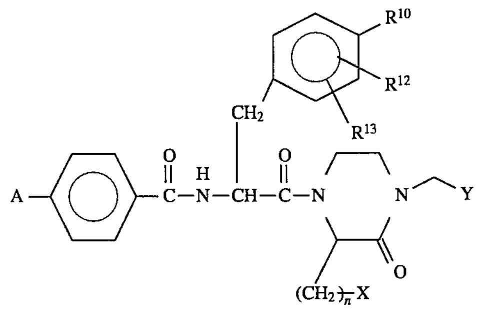

wherein A represents amidino group or an optionally substituted aminoethyl; $R^{10}$ represents one species selected from a group consisting of nitro group, a halogen atom, a lower alkenyl group, a lower alkynyl group, a lower alkyloxycarbonyl group and a group represented by the formula $OR^{11}$ (wherein $R^{11}$ is hydrogen atom or a lower alkyl group, a lower alkenyl group, a lower alkynyl group, a lower alkanoyl group, a carbamoyl group or a methanesulfonyl group, each of which may be substituted; $R^{12}$ and $R^{13}$ respectively represent hydrogen atom, hydroxyl group, a lower alkoxy group or a halogen atom; X represents hydroxyl group, p-hydroxyphenyl group or an optionally esterified or amidated carboxyl group; Y represents an optionally esterified or amidated carboxyl group; and n denotes 1 or 2, or a salt thereof and an agent for inhibiting adhesion of cells which comprise these compounds are desclosed. These have more potent and long lasting activities of inhibiting cell-adhesion, thus being useful as an orally administrable anti-thrombotic agent.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Gly Arg Gly Asp Ser Pro
1 5

2-PIPERAZINONE COMPOUNDS AND THEIR USE

This invention relates to novel 2-piperazinone-1-acetic acid compounds and their salts having an inhibitory activity of adhesion of animal cells, and to agents containing said compounds as the effective component.

The object of the present invention is to provide therapeutic agents of various diseases by, in general, controlling or inhibiting cell-adhesion.

As the factors participating in adhesion to extracellular substrate of animal cells, there have been known fibronectin, vitronectin, osteopontin, collagen, thrombospondin, fibrinogen and von Willebrand factor. These proteins include -Arg-Gly-Asp- as the cell recognition site. This tripeptide is recognized by at least one protein belonging to receptors, integrins, which are heterodimeric proteins consisting of sub-units combined with two membranes (E. Ruoslahti and M. D. Pierschbacher, Science, 238, 491 (1987)).

Structurally related integrins, which recognize the amino acid sequence -Arg-Gly-Asp-, are known to express at extracellular surface of platelets, endothelial cells, leucocyte, lymphocyte, monocyte and granulocyte. Compounds having the amino acid sequence -Arg-Gly-Asp- competitively bind to the site normally bound by intercellular adhesive molecule to thereby inhibit the binding of intercellular adhesive molecules. As such substances for inhibiting intercellular adhesion, there are known, for example, H-Gly-Arg-Gly-Asp-Ser-Pro-OH.

When blood vessels are injured, platelets are activated with, for example, endothelial collagens, which causes binding of fibrinogen to platelets, i.e. platelet aggregation, to form a thrombus. The interaction between platelets and fibrinogen takes place through GP IIb/IIIa, this being an important characteristic feature of platelet aggregation. Cell adhesion-inhibiting substances can inhibit platelet aggregation by interfering with the substances causing platelet aggregation such as thrombin, epinephrine, ADP and collagen.

Besides, cell-adhesion inhibiting substances are expected to be useful as drugs for suppression of metastasis of tumor cells (inhibition of fixed adhesion at the site where the tumor cells are migrated).

Linear or cyclic peptides containing the amino acid sequence, -Arg-Gly-Asp- (RGD) have been known as cell-adhesion inhibiting substances, in, for example, Journal of Biological Chemistry (J. Biol. Chem.), 262, 17294 (1987) and JPA H2(1990)-174797.

These known peptide derivatives mentioned above are not satisfactory in the potency of their activity, and their oral absorbability is not satisfactory. Besides, since these peptide derivatives are hydrolyzed with enzymes including aminopeptidase, carboxypeptidase or various types of endopeptidase, e.g. serineprotease, their stability in a solution containing these enzymes or in a living body is not satisfactory. Therefore, for clinical application of these peptide derivatives, there are problems still to be solved.

On the other hand, non-peptide compounds having an anti-thrombotic action are disclosed in European Patent Application (EPA) Publication No. 483667 [JPA H4(1992)-264068] and EPA Publication No. 505868. Respectively, there are described the compounds having a 4- to 7-membered cyclic alkyleneimino group such as pyrrolidine ring and the compounds having piperidine ring and the like. The compounds having pipazidinone ring and an action of inhibiting cell adhesion is disclosed in EPA Publication No.529858. The compounds having higher potency durable for a longer period, as compared with the above-mentioned known compounds having an anti-thrombotic action, have been sought.

The object of this invention is to provide compounds having a cell adhesion-inhibiting action of higher potency durable for a longer period in a smaller dosage, as compared with known agents for inhibiting cell-adhesion. In other words, the present invention relates to novel 2-piperazinone-1-acetic acid compounds free from the above problems, and to drugs performing cell adhesion-inhibiting effects comprising these compounds as effective components.

More specifically, the present invention relates to the compounds of the formula

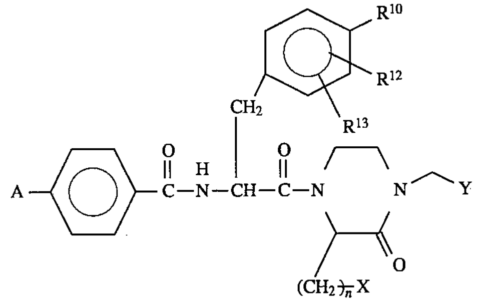

(I)

wherein A represents an amidino group or an optionally substituted aminoethyl group; $R^{10}$ represents one species selected from the group consisting of nitro group, halogen atoms, lower alkenyl groups, lower alkynyl groups, lower alkyloxycarbonyl groups, hydroxymethyl group, formyl group and groups represented by the formula $OR^{11}$ wherein $R^{11}$ is a hydrogen atom or a lower alkyl, a lower alkenyl, a lower alkynyl, a lower alkanoyl, a carbamoyl or a methanesulfonyl group, each of which may be substituted; $R^{12}$ and $R^{13}$ respectively stand for a hydrogen atom, hydroxyl group, a lower alkoxy group or a halogen atom; X stands for hydroxyl group, p-hydroxyphenyl group or an optionally esterified or amidated carboxyl group; Y stands for an optionally esterified or amidated carboxyl group; and n denotes 1 or 2, or salts thereof. [hereinafter, in some instances, these compounds including the salts are called simply Compound (I)], and to cell adhesion-inhibiting agents containing these compounds.

As the representative compounds of the formula (I), mention is made of the compounds of the formula

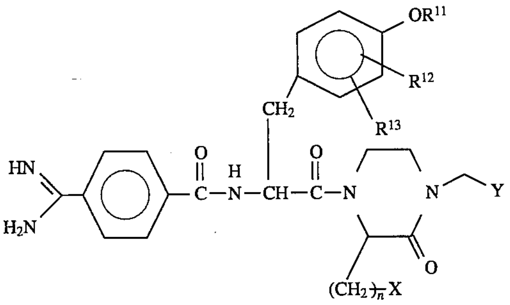

(I')

wherein $R^{11}$ stands for a hydrogen atom, an optionally substituted lower alkyl group, a lower alkanoyl group and an optionally substituted carbamoyl group or methanesulfonyl group; $R^{12}$ and $R^{13}$ respectively stand for a hydrogen atom, hydroxyl group, a lower alkoxy group or a halogen atom; X stands for hydroxyl group, p-hydroxyphenyl group or an optionally esterified or amidated carboxyl group; Y stands for an optionally esterified or amidated carboxyl group; and n denotes 1 or 2 or their salts.

In the formula (I), A represents an amidino group or an optionally substituted aminoethyl group.

As the substituted aminoethyl groups represented by A, preferred are the groups which are capable of removing the removable group therein and converting to physiologically active free amino ethyl group in the body after the compounds (I) having a substituted aminoethyl group are administered as the prodrugs. Examples of the substituent of the amino group in the substituted aminoethyl group include pivaloyloxymethyl, n-octyloxycarbonyl, n-hexyloxycarbonyl, n-octylaminocarbonyl, n-hexylaminocarbonyl, tetrahydrofuran-2-yl, pyrrolidine-1-ylmethyl, morpholinomethyl and N,N-dimethylaminocarbonyloxymethyl.

As the group or atom represented by $R^{10}$ for example, mention is made of a nitro group, halogen atoms, lower alkenyl groups, lower alkynyl groups, lower alkyloxycarbonyl groups and groups bonding via oxygen atom represented by the formula $OR^{11}$. Preferred examples of $R^{11}$ include a hydrogen atom and optionally substituted lower alkyl, lower alkenyl, lower alkynyl, lower alkanoyl, carbamoyl and methanesulfonyl groups.

That is, preferably, $R^{10}$ is one species selected from the group consisting of nitro group, halogen atoms, lower alkenyl groups, lower alkynyl groups, lower alkyloxycarbonyl groups, hydroxymethyl group, formyl group, and groups represented by the formula $OR^{11}$ (wherein $R^{11}$ is a hydrogen atom or lower alkyl, a lower alkenyl, a lower alkynyl, a lower alkanoyl, a carbamoyl and a methanesulfonyl group, each of which may be substituted).

More specifically, the preferred group or atom as $R^{10}$ is one species selected from the group consisting of hydroxy group, $C_{1-5}$ alkoxy groups optionally substituted by $C_{1-3}$ alkoxy groups, $C_{2-3}$ alkenyloxy groups, $C_{2-3}$ alkynyloxy groups, nitro group, halogen atoms, $C_{1-3}$ alkanoyloxy groups, carbamoyloxy groups optionally substituted by $C_{1-3}$ alkyl groups, methanesulfonyloxy group, $C_{2-3}$ alkenyl groups, $C_{2-3}$ alkynyl groups and $C_{1-3}$ alkyloxycarbonyl groups.

Preferable examples of lower alkyl groups represented by $R^{11}$ include straight-chain or branched $C_{1-5}$ alkyl groups such as methyl, ethyl, n-propyl, i-propyl, n-butyl, i-butyl, sec-butyl, tert-butyl, n-pentyl and i-pentyl, among which $C_{1-3}$ alkyl groups are preferred.

Examples of the substituents of "lower alkyl, lower alkenyl, lower alkynyl, lower alkanoyl and methanesulfonyl group, each of which may be substituted" represented by $R^{11}$ include a hydroxyl group, lower ($C_{1-3}$) alkoxyl groups, an amino group, mono-lower ($C_{1-3}$) alkylamino groups, di-lower ($C_{1-3}$) alkylamino groups, lower ($C_{1-3}$) alkanoyl groups, lower ($C_{1-3}$) alkanoyloxy groups, lower ($C_{1-3}$) alkanoylamino groups, lower ($C_{1-3}$) alkoxycarbonyl groups and carbamoyl groups optionally substituted with lower ($C_{1-3}$) alkyl groups. Among them, preferable are lower alkoxy ($C_{1-3}$) groups such as methoxy, ethoxy and propyloxy. Examples of the substituent of carbamoyl group represented by $R^{11}$ includes lower ($C_{1-3}$) alkyl groups.

Preferable examples of lower alkoxy groups represented by $R^{12}$ and $R^{13}$ and lower alkoxy groups included in the substituents of an optionally substituted "lower alkyl group, lower alkenyl, lower alkynyl, lower alkanoyl and methanesulfonyl" represented by the above $R^{11}$ include $C_{1-3}$ alkoxy groups such as methoxy, ethoxy and propoxy.

Preferable examples of lower alkanoyl groups represented by $R^{11}$ and lower alkanoyl groups included in the substituents of an optionally substituted "lower alkyl, lower alkenyl, lower alkynyl, lower alkanoyl and methanesulfonyl groups" represented by $R^{11}$ are $C_{1-3}$ alkanoyl groups such as formyl, acetyl and propionyl.

As halogen atoms represented by $R^{10}$, $R^{12}$ and $R^{13}$, mention is made of fluorine, chlorine, bromine and iodine. Among them, fluorine and chlorine are preferable. Preferable examples of lower alkyl groups as the substituents of an optionally substituted carbamoyl group represented by $R^{11}$ those of lower alkyl groups in lower alkyloxycarbonyl groups represented by $R^{10}$ and those of lower alkyl groups as the substituents of substituted amino group and substituted carbamoyl group as the substituents in optionally substituted lower alkyl, lower alkenyl, lower alkynyl, lower alkanoyl and methanesulfonyl group represented by $R^{11}$, mention is made of $C_{1-3}$ lower alkyl groups such as methyl, ethyl, n-propyl and i-propyl.

Preferable examples of lower alkenyl groups represented by $R^{10}$ and $R^{11}$ are $C_{2-3}$ alkenyl groups such as vinyl, allyl and 1-propenyl.

Preferable examples of lower alkynyl groups represented by $R^{10}$ and $R^{11}$ are $C_{2-3}$ alkynyl groups exemplified by ethynyl and propargyl.

Among the compounds mentioned above, especially preferable are the compounds of the formula (I) wherein $R^{10}$ is a hydroxyl group or methoxy group.

Also preferable are the compounds of the formula (I) wherein $R^{10}$ is an ethoxy group, a methoxyethoxy group, propoxy group, propargyloxy group, allyloxy group, fluorine atom or chlorine atom. Among them, preferable are an ethoxy group, propargyloxy group, allyloxy group and fluorine as $R^{10}$.

With respect to $R^{12}$ and $R^{13}$, preferred are the compounds of the formula (I) wherein both $R^{12}$ and $R^{13}$ are a hydrogen atom.

With regard to n, preferred are the compounds of the formula (I) wherein n denotes 1.

Particularly, among them, preferred are the compounds of the formula (I) wherein A is an amidino group; $R^{10}$ is a hydroxyl group or methoxy group; both $R^{12}$ and $R^{13}$ are a hydrogen atom and n denotes 1.

Also, preferred are the compounds of the formula (I) wherein A is an amidino group; $R^{10}$ is an ethoxy group, propargyloxy group, allyloxy group or fluorine atom; both $R^{12}$ and $R^{13}$ are a hydrogen atom and n denotes 1.

The other preferable compounds are the compounds of the formula (I) wherein A is an aminoethyl group; $R^{10}$ is a hydroxyl group or methoxy group; both $R^{12}$ and $R^{13}$ are a hydrogen atom and n denotes 1.

The other preferable compounds are the compounds of the formula (I) wherein A is an aminoethyl group; $R^{10}$ is an ethoxy group, propargyloxy group, allyloxy group or fluorine atom; both $R^{12}$ and $R^{13}$ are a hydrogen atom and n denotes 1.

As the optionally esterified or amidated carboxyl groups represented by X and Y, preferred are the groups which are convertible in the body after the compound (I) is administered as a prodrug, whereby the compound (I) is converted in a physiologically active form. The optionally esterified or amidated carboxyl groups represented by X and Y are respectively represented by the following formulae,

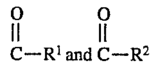

$R^1$ and $R^2$ stand for, independently, a hydroxyl group, $C_{1-8}$ alkoxyl group (e.g. methoxy, ethoxy, propoxy, butoxy), a lower alkenyloxy group, for example, $C_{3-12}$ alkenyloxy group such as allyloxy and butenyloxy, aralkyloxy group (a phenyl lower alkyloxy group whose lower alkyl moiety has about 1 to 4 carbon atoms, such as benzyloxy, phenethyloxy and 3-phenylpropyloxy), or optionally substituted amino groups represented by—$NR^3R^4$ and—$NR^5R^6$. In $NR^3R^4$ and $NR^5R^6$, $R^3$ and $R^4$, and, $R^5$ and $R^6$ independently stand for hydrogen atom, a lower alkyl group ($C_{1-6}$ lower alkyl group such as methyl, ethyl, propyl, butyl and hexyl), $C_{3-8}$ alkenyl group (e.g. allyl, 2-butenyl and 3-pentenyl) or $C_{6-12}$ aralkyl group (e.g. benzyl, phenethyl, phenylpropyl and pyridylmethyl), and the aryl group in aralkyl group may be unsubstituted or substituted with 1 to 2 substituents. Examples of the substituents include nitro, halogen (chlorine, fluorine, bromine), a lower alkyl group (methyl, ethyl, propyl), a lower alkoxyl group (methoxy, ethoxy, propoxy).

The compound (I) of this invention can be formulated into an orally administrable preparation of a prodrug type, and, in this case, it is preferable to introduce, as the above-mentioned $R^1$ and $R^2$, a hydroxyl group, an optionally substituted amino [e.g. amino, N-lower ($C_{1-4}$) alkylamino and N,N-di-lower ($C_{1-4}$) alkylamino)] or an optionally substituted alkoxyl group [e.g. a lower ($C_{1-6}$) alkoxyl group, whose alkyl moiety is optionally substituted with hydroxy or an optionally substituted amino (e.g. amino, dimethylamino, diethylamino, piperidino or morpholino), halogen, a lower ($C_{1-6}$) alkylthio, lower ($C_{1-6}$) alkyloxycarbonyl (e.g. i-butyloxycarbonyl), propylidene, 3-phthalidylidene, an optionally substituted aminocarbonyl, or an optionally substituted dioxolenyl (e.g. 5-methyl-2-oxo-1,3-dioxolen-4-yl)] or a group represented by the formula of—$OCH(R^7)OCOR^8$ [wherein $R^7$ stands for hydrogen atom, a $C_{1-6}$ straight-chain or branched lower alkyl group (e.g. methyl, ethyl, n-propyl, isopropyl, n-butyl, isobutyl, t-butyl, n-pentyl, isopentyl and neopentyl), or a $C_{5-7}$ cycloalkyl group (e.g. cyclopentyl, cyclohexyl or cycloheptyl), and $R^8$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl and neopentyl), a $C_{2-8}$ lower alkenyl group (e.g. vinyl, propenyl, allyl and isopropenyl), a $C_{5-7}$ cycloalkyl group (e.g. cyclopentyl, cyclohexyl and cycloheptyl), a $C_{1-3}$ lower alkyl group substituted with a $C_{5-7}$ cycloalkyl group (e.g. cyclopentyl, cyclohexyl or cycloheptyl) or an aryl group such as a phenyl group (e.g. benzyl, p-chlorobenzyl, phenethyl, cyclopentylmethyl and cyclohexylmethyl), a $C_{2-3}$ lower alkenyl group substituted with a $C_{5-7}$ cycloalkyl group (e.g. cyclopentyl, cyclohexyl or cycloheptyl) or an aryl group such as a phenyl group (e.g. those having an alkenyl moiety such as vinyl, propenyl, allyl or isopropenyl, exemplified by cinamyl), an aryl group such as an optionally substituted phenyl group (e.g. phenyl, p-tolyl and naphthyl), a $C_{1-6}$ straight-chain or branched lower alkoxyl group (e.g. methoxy, ethoxy, n-propoxy, isopropoxy, n-butoxy, isobutoxy, sec-butoxy, t-butoxy, n-pentyloxy, isopentyloxy and neopentyloxy), a $C_{2-8}$ straight-chain or branched lower alkenyloxy group (e.g. allyloxy and isobuteloxy), a $C_{5-7}$ cycloalkyloxy group (e.g. cyclopentyloxy, cyclohexyloxy and cycloheptyloxy), a $C_{1-3}$ lower alkoxyl group substituted with a $C_{5-7}$ cycloalkyloxy group (e.g. cyclopentyl, cyclohexyl and cycloheptyl) or an aryl group such as optionally substituted phenyl (e.g. groups having alkoxy moiety such as methoxy, ethoxy, n-propoxy or isopropoxy, including benzyloxy, phenethyloxy, cyclopentylmethyloxy and cyclohexylmethyloxy), a $C_{2-3}$ lower alkenyloxy group substituted with a $C_{5-7}$ cycloalkyl group (e.g. cyclopentyl, cyclohexyl and cycloheptyl) or with an aryl group such as optionally substituted phenyl (e.g. those having an alkenyloxy moiety such as vinyloxy, propenyloxy, allyloxy or isopropenyloxy, exemplified by cinnamyloxy), or an aryloxy group such as an optionally substituted phenoxy group (e.g. phenoxy, p-nitrophenoxy and naphthoxy)].

Especially, preferable examples of esterified carboxyl groups as the esterified carboxyl group represented by Y in the case of using the compound (I) as a prodrug include—COOMe,—COOEt,—COOtBu,—COOPr, pivaloyloxymethoxycarbonyl, 1-(cyclohexyloxycarbonyloxy)ethoxycarbonyl, 5-methyl-2-oxo-1,3-dioxolen-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy) ethoxycarbonyl, 1-(isobutyryloxy) ethoxycarbonyl, cyclohexylcarbonyloxymethoxycarbonyl, benzoyloxymethoxycarbonyl, cinnmaylocarbonyl, cyclopentylcarbonyloxymethoxycarbonyl, N,N-dimethylcarbonylmethoxy, 2-(isobutyloxycarbonyl)-2-propylideneethoxycarbonyl, (3-phthalidylidene) ethoxycarbonyl.

In the formula (I), as X, among others,—COOH,—$COOCH_3$ and—$CONH_2$ are especially preferable. As Y,—COOH or a group which is convertible to—COOH in the living body is preferable and as n, 1 is preferable.

Excellent in activities are the compounds of the formula (I) wherein, X is—$COOCH_3$, Y is—COOH or groups which are convertible to—COOH in a living body and A, $R^{10}$, $R^{12}$, $R^{13}$ and n are, respectively, one of the above-mentioned preferable groups and atoms.

The compound (I) of this invention has one or more asymmetric carbons in the molecule, and both R-configurated ones and S-configurated ones are included in the present invention.

Incidentally, the compound (I) may be hydrated, and the compound (I) and its hydrate are hereinafter referred to as the compound (I) inclusively.

Examples of the salts of the compound (I) include inorganic acid salts such as hydrochloride, hydrobromide, sulfate, nitrate and phosphate, organic acid salts such as acetate, tartrate, citrate, fumarate, maleate, toluenesulfonate and methanesulfonate, metal salts such as sodium salt, potassium salt, calcium salt and aluminum salt, and salts with a base such as triethylamine salt, guanidine salt, ammonium salt, hydrazine salt, quinine salt and cinchonine salt, which are pharmaceutically acceptable ones.

Specific examples of preferable compounds include
(S)-4-(4-amidinobenzoyl-L-tyrosyl)-3-methoxycarbonylmethyl-2-oxopiperazine-1-acetic acid,
(S)-4-(4-amidinobenzoyl-L-tyrosyl)-3-methoxycarbonylmethyl-2-oxopiperazine-1-acetic acid hydrochloride and
(S)-4-(4-amidinobenzoyl-L-tyrosyl)-3-methoxycarbonylmethyl-2-oxopiperazine-1-acetic acid methanesulfonate,
(S)-4-(4-amidinobenzoyl-O-methyl-L-tyrosyl)-3-methoxycarbonylmethyl-2-oxopiperazine-1-acetic acid,
(S)-4-(4-amidinobenzoyl-O-ethyl-L-tyrosyl)-3-methoxycarbonylmethyl-2-oxopiperazine-1-acetic acid and
(S)-4-{4-(2-aminoethyl)benzoyl-O-methyl-L-tyrosyl}-3-methoxycarbonylmethyl-2-oxopiperazine-1-acetic acid.

The compound (I) of this invention can be produced by, for example, methods as described below. In the following description of the production methods, $R^{10}$, $R^{12}$ and $R^{13}$ in the starting compounds and intermediate compounds may have protecting groups conventionally used in the field of peptide chemistry, and in the following description, these protected groups are included as well. Needless to state, introduction of these functional groups and elimination thereof can be conducted in accordance with conventional means.

The compound (I) can be produced by a) subjecting a compound represented by the formula

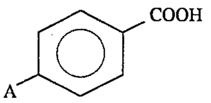
(II)

or

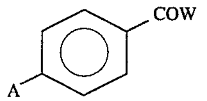
(II')

[wherein W stands for halogen atom] to condensation with a compound represented by the formula

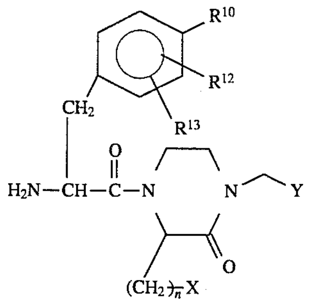
(III)

[wherein each symbol is of the same meaning as defined above ] or b) subjecting a compound represented by the formula

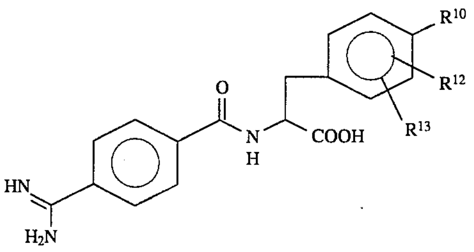
(IV)

[wherein each symbol is of the same meaning as defined above] to condensation with a compound represented by the formula

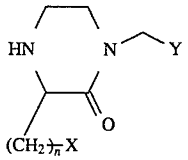
(IV)

[wherein each symbol is of the same meaning as defined above].

The condensation reaction in the above methods a) and b) for producing the compound (I) of this invention can be carried out by an amido-linkage formation reaction in a conventional peptide synthesis, for example, the method using active ester, mixed acid anhydride or acid chloride. For example, the condensation reaction between the compound (II) and the compound (III) or the compound (IV) and the compound (V) can be conducted by subjecting the compound (II) or the compound (IV) to condensation with a phenol such as 2,4,5-trichlorophenol, pentachlorophenol, 2-nitrophenol or 4-nitrophenol or an N-hydroxy compound such as N-succinimide, N-hydroxy-5-norbornen-endo-2,3-dicarboxyimide (HONB), 1-hydroxybenztriazole (HOBT) or N-hydroxypiperidine in the presence of a catalyst such as dicyclohexylcarbodiimide to convert into an active ester thereof, followed by condensation. Alternatively, the compound (II) or the compound (IV) is allowed to react with isobutyl chloroformate to give a mixed acid anhydride, which is then subjected to condensation.

The condensation between the compound (II) and the compound (III) or between the compound (IV) and the compound (V) can also be performed by using singly a peptide-formation reagent such as dicyclohexylcarbodiimide, N,N'-carbonyldiimidazole, diphenylphosphoryl azide or diethyl cyanophosphonate.

In said condensation reaction, the amidino group present in the formula of the compound (II), (II') or (IV) is preferably present as the salt of an inorganic acid (e.g. hydrogen chloride, sulfuric acid, nitric acid or hydrobromic acid) or protected with tert-butoxycarbonyl group or benzyloxycarbonyl group.

Any of the above-mentioned condensation reactions can be promoted by the addition of preferably an organic base (e.g. triethylamine, N-methylpiperidine, 4-N,N-dimethylaminopyridine) or an inorganic base (sodium hydrogencarbonate, sodium carbonate, potassium carbonate). The reaction temperature ranges usually from −20° to +50° C., preferably from 0° C. to about room temperature. Examples of solvents usually employed include water, dioxane, tetrahydrofuran, acetonitrile, pyridine, N,N-dimethylformamide, dimethyl sulfoxide, N-methylpyrrolidone, chloroform and methylene chloride, and these can be used singly or as a mixture.

The protective group of the carboxyl group contained in the product of the above methods (benzyl group or tert-butyl group, which is the protective group of the carboxyl group of X or Y in the general formula (I)) and/or the protective group of phenolic hydroxyl group or alcoholic hydroxyl group (benzyl group or tert-butyl group, which is the protective group of the hydroxyl group of $R^{10}$, $R^{12}$, $R^{13}$ and X in the general formula (I)) can be removed by a per se known method. For example, a compound having a benzyl ester group or a benzyl ether group can be converted to a carboxylic acid derivative by subjecting the compound to hydrogenation in the presence of a precious metal catalyst such as palladium or platinum, and a compound having a tert-butyl ester group or a tert-butyl ether group can be converted to a carboxylic acid derivative by processing the compound with an acid such as trifluoroacetic acid or hydrogen chloride.

While salts of the compound (I) can be obtained by the reaction for producing the compound (I) itself, they can be produced also by adding, upon necessity, an acid, alkali or base.

Thus-obtained object compound (I) of this invention can be isolated from the reaction mixture by a conventional separation and purification means such as extraction, concentration, neutralization, recrystallization, column chromatography and thin-layer chromatography.

In the compound (I), at least two stereoisomers can be present. These individual isomers or a mixture thereof are, as a matter of course, included in the scope of the present invention, and, when desired, these isomers can be produced individually.

By conducting the following reactions using respectively a single isomer of the above-mentioned starting compounds (III), (IV) or (V) and a single isomer of the below-mentioned starting compounds (IX), (X), (XII), (XIII), (XIV) or (XV), a single optical isomer of the compound (I) can be obtained. And, when the product is a mixture of two or more isomers, it can be separated into respective isomers by a conventional separation method, for example, a method of causing formation of a salt with an optically active acid (e.g. camphor sulfonic acid, tartaric acid and dibenzoyl tartaric acid), an optically active base (e.g. cinchonine, cinchonidine, quinine, quinidine, α-methylbenzylamine and dehydroabiethylamine), or various chromatographic means or fractional recrystallization.

The starting compounds (II) and (II') in the present invention are per se known compounds, and the starting compounds shown by the formulae (III), (IV) and (V) can be produced in a manner analogous to per se known methods, and, depending on the case, they can be produced by the methods shown by the following reaction formulae. In the following description, the compound of the formula (III) is, in some instances, simply referred to as (III), and, as to other compounds, the same applies in some instances.

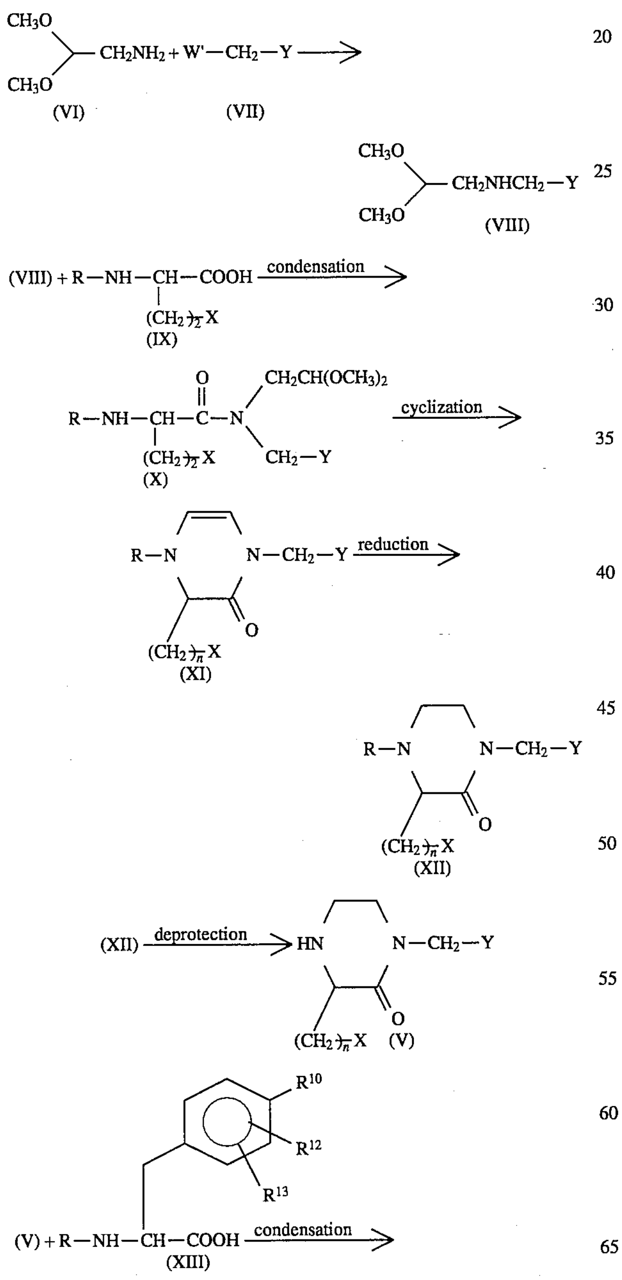

-continued

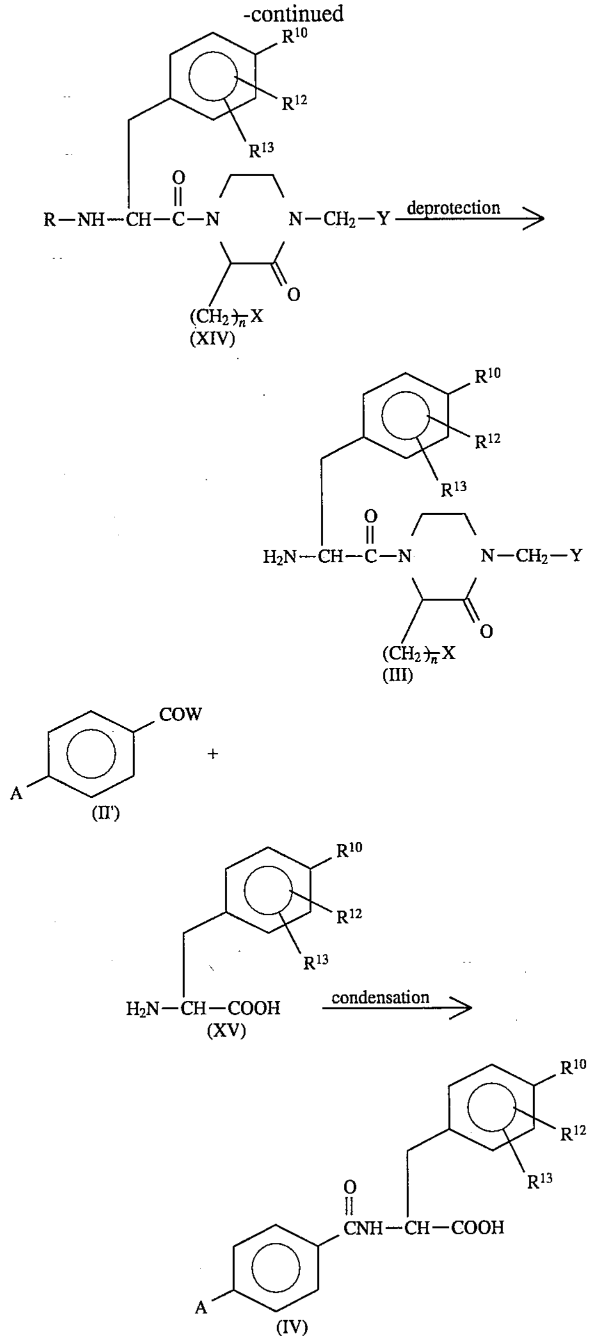

In the above reaction formulae, R is an amino-protective group for an amino acid, and stands for, for example, benzyloxycarbonyl group or tert-butoxycarbonyl group. $R^{10}$, $R^{12}$, $R^{13}$ and X may have a protecting group of phenolic hydroxyl group or alcoholic hydroxyl group. Examples of the protecting group include tert-butyl group and an optionally substituted benzyl group. The carboxyl group of X or Y may have a protective group such as benzyl group or tert-butyl group.

The method of producing the compound (III) shown by the above reaction formulae is explained in further detail. The reaction for obtaining the compound (VIII) by allowing (VI) to react with (VII) is a conventional alkylation of amino group. More specifically stating, the compound (VI) is allowed to react with the compound (VII) usually at temperatures ranging from 0° to +100° C. in the presence of a base (e.g. an inorganic base such as sodium carbonate, potassium carbonate, potassium hydrogencarbonate or cesium fluoride, or an organic base such as triethylamine, pyridine or 4-N,N-dimethylaminopyridine) to give the compound (VIII). As the reaction solvent, mention is made of an organic solvent such as acetonitrile, N,N-dimethylformamide, tetrahydrofuran, toluene and methylene chloride.

The subsequent production of the compound (X) by subjecting the compound (VIII) to condensation with the N-protected derivative of amino acid is performed by a conventional reaction for peptide-linkage formation reaction of amino acid. The compound (X) can be produced under substantially the same reaction conditions as those in the condensation of the compound (II) with the compound (III).

Cyclization of the thus-obtained compound (X) into the cyclic compound (XI) is the cyclization reaction with an acid catalyst. As the catalyst, use is made of, for example, an organic sulfonic acid such as p-toluenesulfonic acid, camphorsulfonic acid and methanesulfonic acid. The reaction is conducted by subjecting the compound (X) to reaction usually in a solvent such as toluene, benzene, ethyl acetate or 1,2-dichloroethane at temperatures ranging from 0 to 100° C., preferably from +30° to +80° C. to give the compound (XI).

The subsequent reduction of the compound (XI) to the compound (XII) is a reaction for reducing a double bond, and the compound (XII) can be readily produced by, for example, catalytic reduction using, as the catalyst, a metal such as platinum, palladium or Raney nickel, or a mixture of them with an optional carrier, or a reduction using a metallic hydride, for example, sodium borohydride or sodium cyano borohydride. The above reactions are conducted usually in the presence of an organic solvent (e.g. methanol, ethanol, dioxane, ethyl acetate). While the reaction temperature varies with the means of reduction, preferable range is, in general, from about −20° to about +100° C. While this reaction proceeds satisfactorily under normal pressure, it may be conducted, depending on cases, under elevated pressure. When R is benzyloxycarbonyl group and the reduction is conducted catalytically, the reaction of removing the protective group of R proceeds simultaneously and the compound (V) can be obtained at one stroke.

Reactions for removing protective groups in (XII) to (V) and (XIV) to (III) are conventional reactions for removing protective groups of amino groups in peptide, and, in the case where R stands for a benzyloxycarbonyl group, the protective group can be removed by catalytic reduction using, as the catalyst, a metal such as platinum, palladium or rhodium. And, when R stands for tert-butoxy carbonyl group, the protective group can be easily removed by the use of an acid such as trifluoroacetic acid or hydrogen chloride in an organic solvent such as methanol, ethanol, ethyl acetate or dioxane.

The condensation reaction of the compound (V) with an amino acid derivative (XIII) and that of the compound (II') with the compound (XV) are reactions for forming amido-linkage. These reactions can be conducted in substantially the same manner as in the condensation of the compound (II) with the compound (III).

The starting compounds represented by the formula (XIII) can be produced by, for example, analogous methods to that disclosed in J. Am. Chem. Soc., 77 (1955). To state further, in general, the compound (XIII) whose $R^{10}$ is respectively a substituted lower alkyloxy, a lower alkenyloxy, a lower alkynyloxy, a lower alkanoyloxy, carbamoyloxy or alkylsulfonyloxy can be produced by allowing tyrosine or 3,4-dihydroxyphenylalanine (DOPA) whose amino group is protected with benzyloxycarbonyl group or tertbutoxycarbonyl group, to react with dialkyl sulfate such as dimethyl sulfate or diethyl sulfate, or alkyl halide, acid anhydride, alkylisocyanate, alkylsulfonyl halide or the like. The reaction can be conducted in the presence of a base (e.g. an inorganic base including sodium hydroxide, potassium hydroxide, sodium carbonate, potassium carbonate, sodium hydrogencarbonate and cesium fluoride, or an organic base including triethylamine, pyridine, 4-N,N-dimethylaminopyridine or the like), usually at temperatures ranging from about 30° to about 100° C. As the reaction solvent, use is made of, for example, acetonitrile, N,N-dimethylformamide, tetrahydrofuran, toluene, methylene chloride or the like.

And, the compound (XIII) whose $R^{10}$ stands for a lower alkenyl group, a lower alkynyl group or a lower alkyloxycarbonyl group can be produced in accordance with a per se known method, namely, the method disclosed in {J. Chem. Soc., Chem. Commun., 904 (1987), J. Am. Chem. Soc., 109, 547 (1987) or J. Org. Chem., 48, 3252 (1983)}.

Among the compounds represented by the formula (XIII), those wherein $R^{10}$ stands for nitro group or a halogen atom, and $R^{12}$ and $R^{13}$ respectively stands for hydrogen atom. use can be made of known compounds commercially available.

In general, the compound represented by the formula (XIII) can be produced by substantially the same method employable for the synthesis of alpha-amino acid, for example, J. Am. Chem. Soc., 70, 1451 (1948), Proc. Chem. Soc., 117 (1962) and J. Am. Chem. Soc., 65, 2211 (1943). To state further, respective optical isomers of the compounds represented by the formula (XIII) can be produced by substantially the same methods disclosed in known literature references, for example, U.S. Pat. No. 3841966 (1949).

Among the compounds represented by the formula (XIV), the compound whose $R^{10}$ is formyl group can be produced by subjecting the compound (XIV) whose $R^{10}$ is vinyl group to oxidation with ruthenium tetroxide. Among the compounds represented by the formula (XIV), a compound whose $R^{10}$ is hydroxymethyl group can be produced by subjecting the compound (XIV) wherein $R^{10}$ is formyl group to reduction with sodium borohydride.

Among the compounds represented by the formula (XIV), a compound wherein Y stands for an esterified carboxyl group employable as a prodrug can be produced substantially in accordance with the method known by literature references, namely, Chem. Pharm. Bull., 31, 2698 (1983), Chem, Pharm, Bull., 32, 2241 (1984), J. Antibiotics, 40, 81 (1987), J. Antibiotics, 45, 1358 (19920), among others. To state further, in general, the said compound can be produced by allowing the compound (XVI) wherein Y is carboxyl group to react with a known halogenated organic compound disclosed in, for example, {Chem. Pharm. Bull., 31, 2698 (1983), Chem. Pharm. Bull., 32, 2241 (1948), J. Antibiotics, 40, 81 (1987), and J. Antibiotics, 45, 1358 (1992)} in the presence of a base (e.g. an inorganic base such as sodium hydroxide, potassium hydroxide, sodium carbonate, potassium carbonate, sodium hydrogencarbonate or cesium fluoride, or an organic base such as triethylamine, pyridine or 4-N,N-dimethylaminopyridine, usually at temperatures ranging from −20° to 100° C. As the reaction solvent, mention is made of N,N-dimethylformamide, acetonitrile, methylene chloride ethyl acetate, tetrahydrofuran or the like.

In the above-mentioned methods of producing the compound (I) and its intermediates, the compounds to be employed for the reactions may, unless undesirable effects are brought about, be in the forms of salts, for example, an inorganic acid salt such as hydrochloride, hydrobromide, sulfate, nitrate or phosphate, an organic acid salt such as acetate, tartrate, citrate, fumarate, maleate, toluenesulfonate or methanesulfonate, a metal salt such as sodium salt, potassium salt, calcium salt or aluminum salt, and a salt with a base such as triethylamine salt, guanidine salt, hydrazine salt, quinine salt or cinchonine salt.

When the compound (I) is obtained in a free form by the above-mentioned production method, it can be converted to a salt thereof by a conventional method, and when a salt of the compound (I) is obtained, it can be converted to the compound (I) by a conventional method.

The compounds of the formula (I) (including their hydrates) are low in toxicity and are used safely, and they inhibit both the binding of fibrinogen, fibronectin and yon Willebrand factor to the fibrinogen receptor of blood platelets (Glycoprotein IIb/IIIa) and the various types of bindings of the above-mentioned adhesive proteins and other adhesive proteins, such as vitronectin collagen and laminin, to the corresponding receptors on the surface of cells.

Hence, the compounds of this invention exert influence on cell-cell and cell-matrix interactions. They prevent, in particular, the development of blood platelet thrombin and can be used in the therapy or prophylaxis of diseases such as peripheral arterial obstruction, acute myocardial infarction (AMI), deep vein thrombosis, pulmonary embolism, dissecting aneurysm, transient ischemic attack (TIA), cerebral apoplexy and other occlusive diseases, unstable angina, disseminated intravascular coagulation (DIC), sepsis, surgical or infective shock, postoperative and postdelivery trauma, cardiopulmonary bypass surgical operation, incompatible blood transfusion, amotio placentae, thrombotic thrombocytopenic purpura (TTP), acute or chronic renal diseases caused by hyper-agglutination such as snake venom and immunological diseases, inflammations, arteriosclerosis, hemolytic uremic syndrome, symmetric peripheral necrosis and decubitus in mammals including humans.

Further, the compound (I) of this invention can be used for enhancing the action of a thrombolytic agent and for preventing re-obstruction, preventing re-obstruction after PTCA, preventing thrombocytopenia, and preventing thrombus caused by artificial blood vessel and organs, and, besides, it inhibits metastasis and can be used as an antitumor agent.

Medicinal compositions containing compounds of the formula (I) (including their hydrates and salts) can be administered, for example, orally in the form of tablets, lacquered tablets, sugar-coated tablets, hard and soft gelatin capsules, solutions, emulsions or suspensions, or rectally, for example, in the form of suppositories, or as spray. The preparations in the above-mentioned various forms can be produced respectively in a conventional method, if necessary with the use of excipients and the like. However, administration can also be performed non-orally, for example in the form of injectable solutions.

To prepare tablets, lacquered tablets, sugar-coated tablets and hard gelatin capsules, the active compound can be mixed with pharmaceutically acceptable inorganic or organic excipients. Typical examples of such excipients, which can be used for tablets, sugar-coated tablets and hard gelatin capsules, include lactose, corn starch or derivatives thereof, talc, and stearic acid or salts thereof. Examples of suitable excipients for soft gelatin capsules are vegetable oil, wax, fat, and, semisolid or liquid polyol. However, no excipients whatever are necessary with soft gelatin capsules when the characteristic features of the active compound are appropriate.

Examples of suitable excipients for the preparation of solutions and syrupy preparations are water, polyol, sucrose, invert sugar and glucose. Examples of suitable excipients for injectable solutions are water, alcohol, polyol, glycerol and vegetable oil.

Suitable examples for suppositories are natural or hardened oil, wax, fat and semiliquid or liquid polyol. The pharmaceutical compositions can additionally contain a preservative, a solubilizer, a stabilizer, a wetting agent, an emulsifier, a sweetener, a colorant, a flavoring, a salt to alter the osmotic pressure, a buffer, a coating agent or an antioxidant.

The dosage of the active compound for controlling or preventing the diseases referred to hereinbefore can vary within a wide range and should, of course, be adjusted to suit the individual circumstances in each particular case. In general, a dose of about 0.01 to 20 mg/kg, preferably about 0.1 to 4 mg/kg, per day is appropriate on oral administration for adults. When administered non-orally, preferable daily dosage per adult is about 0.005 to 1.0 mg/kg, preferably about 0.01 to 0.3 mg/kg.

The present invention provides the compounds and medicinal products effective for prophylaxis and therapy of various diseases by controlling or preventing cell-adhesion. Especially, the compound of this invention performs controlling, over a long period of time, of platelet aggregation caused by ADP, by oral administration, and, therefore, it can be used as an antithrombotic agent which is more potent and longlasting as compared with known substances having similar activities.

The following test examples, reference examples and working examples will describe the present invention in further detail, but they are not intended to limit the present invention in any way.

TEST EXAMPLE 1

Binding Experiment in Vitro

Method

Washed platelets were prepared from sodium citrate—supplemented blood of guinea pig, which were suspended in a Hepes Tyrode solution (pH 7.5) to adjust the number of platelets to be 500,000/μl. To 70 μl of this suspension was added 10 μl of an ADP solution (final concentration: $5\times10^{-5}$M), and the mixture was left standing for 15 minutes at room temperature. To the mixture were added a solution of the test drug and 80 μl of a $^{125}$I-fibrinogen solution (final concentration: 0.1 μM), which was left standing for 2 hours at room temperature. Onto a 20% sucrose buffer solution was overlaid 100 μl of the reaction mixture, which was subjected to centrifuge at 3,000 rpm to separate platelet-adhesive $^{125}$I-fibrinogen from non-adhesive one. The radioactivity of the platelet-adhesive $^{125}$I-fibrinogen was determined. From the value obtained from the test groups against specific binding of the control group (processed with the buffer solution), the adhesion inhibiting ratio was determined.

Action of the compound of Working Example 1 against the specific binding of $^{125}$I-fibrinogen to activated platelets of guinea pigs.

$IC_{50}$ value: $2.7\times10^{-9}$M (n=3; n means the number of test animals. In the following Test Examples, n has the same meaning.)

TEST EXAMPLE 2

Determination of Platelet Aggregation in Vitro

Method

In the case of humans, blood was collected from brachial vein of healthy male volunteers who had been administered with no drug for at least two weeks, and in the case of guinea pigs, blood was collected from abdominal aorta under anesthesia with pentobarbital (20 mg/kg, i.p.) using sodium citrate as an anticoagulant (final concentration: 0.38% in the case of humans; 0.315% in the case of guinea pigs). The sodium citrate—supplemented blood was centrifuged at 950 rpm for 10 minutes and 2,000 rpm for 10 minutes respectively at room temperature to obtain platelet rich plasma (PRP) and platelet poor plasma (PPP). PRP was diluted with PPP to adjust the number of platelets to be 500,000/μl. Platelet aggregation measured spectroscopically in accordance with Born's method (Nature 194: 927, 1962) using an aggregometer (HEMA TRACER VI Toa Iyo Denshi). The PRP (250 μl) was incubated at 37° C. for 2 minutes, to which was then added 25 μl of a test drug solution. Two minutes later, 25 μl of an agent for causing agglutination. The effect of the test drug was shown by the inhibition rate of the maximum aggregation rate of the test group against that of the control group. ADP was used in the minimum concentration (0.6–1 μM) capable of obtaining maximum aggregation.

Inhibitory effect on platelet aggregation by ADP of the compounds of Working Examples

| Working Example | Inhibition of platelet aggregation by ADP, $IC_{50}$(M) | |
|---|---|---|
| (W.E) No. | human (n = 3) | guinea pigs (n = 3) |
| 1 | $2.0 \times 10^{-8}$ | $3.7 \times 10^{-8}$ |
| 3 | $1.0 \times 10^{-8}$ | $1.5 \times 10^{-8}$ |
| 4 | — | $1.2 \times 10^{-7}$ |
| 5 | $4.0 \times 10^{-8}$ | $3.4 \times 10^{-8}$ |
| 14 | $1.6 \times 10^{-8}$ | $3.3 \times 10^{-8}$ |
| 18 | $2.0 \times 10^{-8}$ | $2.6 \times 10^{-8}$ |
| 19 | $2.1 \times 10^{-8}$ | $2.2 \times 10^{-8}$ |
| 21 | $2.6 \times 10^{-8}$ | $3.8 \times 10^{-8}$ |
| 22 | $1.8 \times 10^{-8}$ | $4.7 \times 10^{-8}$ |
| 23 | $1.7 \times 10^{-8}$ | $3.8 \times 10^{-8}$ |
| 24 | $2.4 \times 10^{-8}$ | $4.6 \times 10^{-8}$ |
| 31 | $1.2 \times 10^{-8}$ | $1.8 \times 10^{-8}$ |

(— not measured yet)

TEST EXAMPLE 3

Ex Vivo Platelet Aggregation Experiment

Method

After fasting overnight, guinea pigs were orally administered with a test drug solution (2 ml/kg). Blood was collected from the animals, under anesthesia with pentobarbital, after 1, 4 and 24 hours respectively. By the method described above, PRP was prepared and the platelet aggregation caused by ADP was measured. The rate of inhibition of aggregation was determined by the aggregation rate obtained in the test groups against that obtained in the control. The test drug was administered orally as a solution in distilled water. ADP aggregation inhibiting action by the compound of working Example 1 in guinea pigs 3 mg/kg p.o. after 1 hour inhibition rate: 100% (n=4)
3 mg/kg p.o. after 4 hour inhibition rate: 100% (n=4)
3 mg/kg p.o. after 24 hour inhibition rate: 100% (n=3) ADP aggregation inhibiting action by the compound of Working Example 3 in guinea pigs
1 mg/kg p.o. after 1 hour inhibition rate: 95% (n=6)
1 mg/kg p.o. after 4 hour inhibition rate: 100% (n=6)

REFERENCE EXAMPLE 1

N-(2,2-Dimethoxyethyl)Glycine Tert-Butyl Ester

To a mixture of 150 g of 2,2-dimethoxyethylamine, 200 g of anhydrous potassium carbonate and 1.4 liter of N,N-dimethylformamide was added 100 ml of tert-butyl choloroacetate. while stirring at temperatures ranging from 20° to 25° C. After stirring for 2 hours, 100 ml of tert-butyl choloroacetate was added to the mixture, which was stirred for 7 hours at temperatures ranging from 20° to 25° C. To the reaction mixture was added 1.4 liter of ice-water, which was subjected to extraction with ethyl acetate. The organic layer was washed with a saturated aqueous saline solution and dried over anhydrous sodium sulfate, followed by distilling off the solvent under reduced pressure. The residue was subjected to distillation under reduced pressure to give a fraction whose boiling point was 80°–85° C. (0.4 mm Hg) as the object product. The yield was 163 g. NMR spectrum ($CDCl_3$) δ: 1.49 (s, 9 H), 2.75 (d, J=5.4 Hz, 2H), 3.33 (s, 2H), 3.39 (s, 6H), 4.47 (t, J=5.4 Hz, 1H)

REFERENCE EXAMPLE 2

(S)-3-Methoxycarbonylmethyl-2-Oxopiperazine-1-Acetic Acid Tert-Butyl Ester Oxalate To a solution of 44 g of N-(2,2-dimethoxyethyl) glycine tert-butyl ester and 49.5 g of N-benzyloxycarbonyl-L-aspartic acid beta-methyl ester in 400 ml of methylene chloride was added, while stirring under ice-cooling, 44 g of 1-ethyl-3-(3-dimethylaminopropyl) carbodiimide. The mixture was stirred for 10 minutes under ice-cooling, then for 50 minutes at room temperature. To the reaction mixture were added 300 ml of water and 100 ml of a 5% aqueous solution of $KHSO_4$, which was shaken. The organic layer was separated, and the aqueous layer was subjected to extraction with 200 ml of methylene chloride. The organic layers were combined, washed with water and dried over anhydrous sodium sulfate, followed by distilling off the solvent under reduced pressure. The residue (88 g) was dissolved in one liter of toluene, to which was added 4.0 g of p-toluenesulfonic acid, followed by stirring for 4 hours at 70°–75° C. The reaction mixture was cooled, which was washed with an aqueous solution of sodium hydrogencarbonate, dried over anhydrous sodium sulfate, and then the solvent was distilled off under reduced pressure. The residue was subjected to a silica gel (600 ml) column chromatography. Fractions eluted with one liter of the eluent (ethyl acetate-hexane=1:1) were combined and concentrated under reduced pressure. To a solution of the residue (68 g) in 1.5 liter of ethyl acetate was added 16 g of 10% palladium-carbon. The mixture was stirred vigorously for 3 hours in hydrogen streams. The catalyst was filtered off. To the filtrate was added a solution of 20.2 g of oxalic acid dihydrate in 200 ml of methanol, and the mixture was left standing. Resulting crystalline precipitate was collected by filtration, washed with ethyl acetate and dried to afford 46.8 g of the object compound, m.p.146°–147° C. Specific rotation $[\alpha]_D^{23}$–26.0° (c=0.603, methanol) Elemental Analysis for $C_{13}H_{22}N_2O_5.C_2H_2O_4$ :

Calcd.: C, 47.87; H, 6.43; N, 7.44

Found: C, 47.79; H, 6.20; N, 7.42

REFERENCE EXAMPLE 3

(S)-4-L-Tyrosyl-3-Methoxycarbonylmethyl-2-oxopiperazine-1Acetic Acid Tert-Butyl Ester Acetate In 15 ml of dichloromethane were dissolved 1.65 g of (S)-3-methoxycarbonylmethyl-2-oxopiperazine-1-acetic acid tert-butyl ester and 1.9 g of N-benzyloxycarbonyl-L-tyrosine. To the solution was added, while stirring for one hour, 1.44 g of 1-ethyl-3-(3-dimethylaminopropyl) carbodiimide hydrochloride, and the mixture was stirred for one hour. The reaction mixture was concentrated under reduced pressure to leave an oily substance, which was dissolved in ethyl acetate. The organic layer was washed with a 5% aqueous solution of potassium hydrogen carbonate and dried over anhydrous magnesium sulfate, followed by distilling off the solvent under reduced pressure. The residue was subjected to a silica gel column chromatography (eluent: ethyl acetate: hexane=7:3) to afford 2.0 g of (S)-4-(N-benzyloxycarbonyl-L-tyrosyl)-3-methoxycarbonylmethyl-2-oxopiperazine-1-acetic acid tert-butyl ester as a colorless oily product. IR $\gamma_{max}$ $cm^{-1}$ : 3332, 2952, 1740, 1646, 1613, 1514, 1444, 1367, 1227, 1153. NMR($CDCl_3$) δ: 1.46(9H,s), 2.30–2.53(1H,m), 2.72–3.13(5H,m), 3.50–3.72(2H,m), 3.63(3H,s), 3.85(1H,d,J=12 Hz), 4.07(1H,d,J=12 Hz), 4.70–4.90(1H,m), 4.90–5.05(1H,m), 5.11(2H,s), 5.50–5.67(2H,m), 6.76(2H,d,J=8.2 Hz), 7.03(2H,d,J=8.2 Hz), 7.36(5H,s).

A mixture of 1.3 g of (S)-4-(N-benzyloxycarbonyl-L-tyrosyl)-3 -methoxycarbonylmethyl-2-oxopiperazine-1-acetic acid tert-butyl ester thus obtained, 300 mg of 10% palladium-carbon, 180 mg of acetic acid and 20 ml of methanol was stirred for 30 minutes in hydrogen streams. The catalyst was filtered off, and the filtrate was concentrated under reduced pressure to afford 1.0 g of (S)-4-L-tyrosyl-3-methoxycarbonylmethyl-2-oxo-piperazine-1-acetic acid tert-butyl ester acetate as a colorless oily product. This product can be used in the subsequent reaction without purification.

WORKING EXAMPLE 1

(S)-4-(4-Amidinobenzoyl-L-Tyrosyl)-3-Methoxycarbonylmethyl-2-Oxopiperazine-1-Acetic Acid Hydrochloride In a mixture solution of 20 ml of water and 10 ml of dioxane were dissolved 1.0 g of (S)-4-L-tyrosyl-3-methoxycarbonylmethyl-2-oxopiperazine-1-acetic acid tert-butyl ester and 380 mg of sodium hydrogencarbonate. To the solution was added, while stirring vigorously, 505 mg of 4-amidinobenzoyl chloride hydrochloride, over a period of 10 minutes. The mixture was stirred for one hour, then the reaction mixture was concentrated under reduced pressure. To the concentrate was added 10 ml of trifluoroacetic acid, and the mixture was stirred for one hour. The reaction mixture was concentrated to dryness under reduced pressure, which was dissolved in 5 ml of 1N HCl. The solution was subjected to a Wakogel LP-C18 column (eluent: a 7.5% aqueous solution of acetonitrile). The object fractions were collected and lyophilized to afford 550 mg of the object compound as a colorless powdery product.

Specific rotation: $[\alpha]_D^{23}$+91° (c=0.2, $H_2O$)

Elemental Analysis for $C_{26}H_{29}N_5O_8$.HCl (576.0):

Calcd.: C, 54.22; H, 5.25; N, 12.16

Found: C, 53.94; H, 5.31; N, 11.93

REFERENCE EXAMPLE 4

(S)-4-O-$^t$Butyl-L-Tyrosyl-3-Methoxycarbonylmethyl-2-Oxopiperazine-1-Acetic Acid Tert-Butyl Ester Acetate In substantially the same manner as in Reference Example 3, 1.87 g of (3)-methoxycarbonylmethyl-2-oxopiperazine-1-acetic acid tert-butyl ester and 2.43 g of N-benzyloxycarbonyl-O-$^t$butyl-L-tyrosine were processed to give 3.2 g of (S)-4-(N-benzyloxycarbonyl-O-$^t$butyl-L-tyrosyl)-3-methoxycarbonylmethyl-2-oxopiperazine-1-acetic acid tert-butyl ester as a colorless oily product.

IR $\gamma_{max}$$cm^{-1}$ : 3300. 2980. 1740, 1655, 1505, 1440, 1365, 1237, 1160.

NMR($CDCl_3$) δ:1.31(9H,s), 1.46(9H,s), 2.35–2.51(1H,mu), 2.70–3.18(5H,m), 3.57–3.70(2H,m), 3.63(3H,s), 3.81(1H,d,J=17 Hz), 4.02(1H,d,J=17 Hz), 4.75–4.88(1H, mu), 5.00(2H,t,J=5.2 Hz), 5.10(2H,s), 5.65(1H,d,J=8.8 Hz), 6.91(2H,d,J=8.4 Hz), 7.10(2H,d,J=8.4 Hz), 7.35(5H, s).

A mixture of 3.2 g of thus-obtained (S)-4-(N-benzyloxycarbonyl-O-$^t$butyl-L-tyrosyl)-3-methoxycarbonylmethyl-2-oxopiperazine-1-acetic acid tert-butyl ester, 1.0 g of 10% palladium carbon, 300 mg of acetic acid and 50 ml of methanol was stirred for 30 minutes in hydrogen streams. The catalyst was filtered off. The filtrate was concentrated under reduced pressure to leave 2.80 g of the object compound as a colorless oily product. This product can be used as it is for the subsequent reaction.

WORKING EXAMPLE 2

(S)-4-(4-Amidinobenzoyl-L-Tyrosyl)-3-Methoxycarbonylmethyl-2-Oxopiperazine-1-Acetic Acid In a mixture solution of 40 ml of water and 20 ml of dioxane, were dissolved 2.80 g of (S)-4-O-$^t$butyl-L-tyrosyl-3-methoxycarbonylmethyl-2-oxopiperazine-1-acetic acid acetate obtained in Reference Example 4 and 840 mg of sodium hydrogencarbonate. To the solution was added, while stirring vigorously, 1.1 g of 4-amidinobenzoyl chloride hydrochloride, over 20 minutes. The reaction mixture was concentrated under reduced pressure to give a crude product, which was dissolved in 30 ml of trifluoroacetic acid. The solution was left standing for one hour, followed by concentration under reduced pressure. The concentrate was purified by using MCI GEL CHP 20P column (10% aqueous solution of acetonitrile). The fraction containing the object compound was concentrated, which was recrystallized from water-methanol to afford 1.9 g of the object compound as colorless crystalline product, m.p.229–235° C.

Specific rotation: $[\alpha]_D^{20}$+82° (c=1.0, $H_2O$)

Elemental Analysis for $C_{26}H_{29}N_5O_8$.3/2$H_2O$:

Calcd.: C, 55.12; H, 5.69; N, 12.36

Found: C, 55.38; H, 5.66; N, 12.40.

REFERENCE EXAMPLE 5

(S)-4-O-Methyl-L-Tyrosyl-3-Methoxycarbonylmethyl-2-Oxopiperazine-1-Acetic Acid Tert-butyl Ester Acetate In substantially the same manner as in Reference Example 3, (S)-3-methoxycarbonylmethyl-2-oxopiperazine1-acetic acid tert-butyl ester obtained in Reference Example 2 and N-benzyloxycarbonyl-O-methyl-L-tyrosine were subjected to condensation. The condensate was subjected to catalytic reduction to afford (S)-4-O-methyl-L-tyrosyl-3-methoxycarbonylmethyl-2-oxopiperazine-1-acetic acid tert-butyl ester acetate as a colorless oily product. The yield was 85%.

In substantially the same manner as above, the following compounds of Reference Examples 6 to 9 were obtained as colorless oily products

TABLE 1

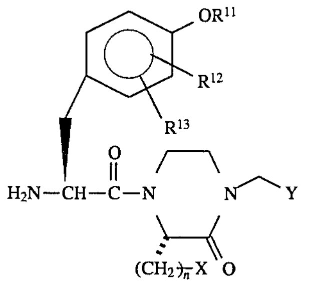

| Reference Example (R. Ex.) No | $R^{11}$ | $R^{12}$ | $R^{13}$ | n | X | Y |
|---|---|---|---|---|---|---|
| 6 | $C_2H_5$ | H | H | 1 | $COOCH_3$ | $COO^tBu$ |
| 7 | n-$C_3H_7$ | H | H | 1 | $COOCH_3$ | $COO^tBu$ |
| 8 | i-$C_3H_7$ | H | H | 1 | $COOCH_3$ | $COO^tBu$ |
| 9 | n-$C_4H_9$ | H | H | 1 | $COOCH_3$ | $COO^tBu$ |

REFERENCE EXAMPLE 10

(S)-4-L-3,4-Dimethoxyphenylalanyl-3-Methoxycarbonylmethyl-2-Oxopiperazine-1-Acetic Acid Trifluoroacetate (S)-3-methoxycarbonylmethyl-2-oxopiperazine-1-acetic acid tert-butyl ester and N-tert-butoxycarbonyl-L-3, 4-dimethoxyphenylalanine were condensed, which was allowed to react with trifluoroacetic acid in methylene chloride. The solvent was distilled off under reduced pressure to leave the object compound as a colorless oily product. This product can be used for the subsequent reaction without purification.

REFERENCE EXAMPLE 11

(S)-4-L-3,4-Diethoxyphenylalanyl-3-Methoxycarbonylmethyl-2-Oxopiperazine-1-Acetic acid Trifluoroacetate In substantially the same manner as in Reference Example 10, The title compound can be produced from (S)-3-methoxycarbonylmethyl-2-oxopiperazine-1-acetic acid tert-butyl ester and N-tert-butoxycarbonyl-L-3,4-diethoxyphenylalanine.

REFERENCE EXAMPLE 12

(S) -3-Tert-Butoxymethyl-2-Oxopiperazine-1-Acetic Acid

In substantially the same manner as in Reference Example 2, the title compound was synthesized from N(2,2-dimethoxyethyl) glycine tert-butyl ester and N-benzyloxycarbonyl-O-tert-butyl-L-serine. M.p. 178°–180° C.

Specific rotation $[\alpha]_D^{20}$–30.4° (c=1.0, DMSO)

Elemental Analysis for $C_{15}H_{28}N_2O4.C_2H_2O_4.0.5H_2O$:

Calcd.: C, 51.12; H, 7.82; N, 7.01

Found: C, 51.40; H, 7.71; N, 6.94

REFERENCE EXAMPLE 13

(S)-3-(4-Tert-Butoxybenzyl)-2-Oxopiperazine-1-Acetic Acid Tert-Butyl Ester

In substantially the same manner as in Reference Example 2, the title compound was synthesized from N-(2,2-dimethoxyethyl)glycine and N-benzyloxycarbonyl-O-tert-butyl-L-tyrosine. M.p.124°–126° C.

Specific rotation $[\alpha]_D^{20}$–81.7° (c=0.97, $CHCl_3$)

Elemental Analysis for $C_{21}H_{32}N_2O_4$ :

Calcd.: C, 66.99; H, 8.57; N, 7.44

Found: C, 66.92; H, 8.54; N, 7.38

The compounds obtained in Reference Example 12 and Reference Example 13 were respectively condensed with N-benzyloxycarbonyl-O-tert-butyl-L-tyrosine in substantially the same manner as in Reference Example 3, followed by catalytic reduction to afford the compounds of Reference Example 14 and Reference Example 15, respectively.

REFERENCE EXAMPLE 14

(S)-4-O-Tert-Butyl-L-Tyrosyl-3-Tert-Butoxymethyl-2-Oxopiperazine-1-Acetic Acid Tert-Butyl Ester Acetate

REFERENCE EXAMPLE 15

(S)-4-O-Tert-Butyl-L-Tyrosyl-3-(4-Tert-Butoxybenzyl)-2-Oxopiperazine-1-Acetic Acid Tert-Butyl Ester Acetate

Working Example 3

(S)-4-(4-Amidinobenzoyl-O-Methyl-L-Tyrosyl)-3-Methoxycarbonylmethyl-2-Oxopiperazine-1 -Acetic Acid In substantially the same manner as in Working Example 2, (S)-4-0-methyl-L-tyrosyl-3-methoxycarbonylmethyl-2 -oxopiperazine-1 -acetate tert-butyl ester obtained in Reference Example 5 was condensed with 4-amidinobenzoylchloride, followed by deprotection by using trifluoroacetic acid. The resulting compound was purified by means of MCI GEL CHP20P column (Mistsubishi Chemical Industries, Ltd. ) (eluent: $H_2O \rightarrow 5\%CH_3CN \rightarrow 10\%CH_3CN$), followed by recrystallization from water—ethanol to afford the object compound as a colorless crystalline product. The yield was 66% ). M.p. 208°–212° C.

Specific rotation $[\alpha]_D^{20}$–76.7° (c=1.035, DMSO)

Elemental Analysis for $C_{27}H_{31}N_5O_8.3H_2O$:

Calcd.: C, 53.37; H, 6.14; N, 11.53

Found: C, 53.15; H, 6.14; N, 11.36

In substantially the same manner as above, the following compounds of Working Examples 4 to 11 were obtained from the compounds respectively obtained in Reference Examples 5, 6, 7, 8, 9, 10, 11, 14, 15 and 4amidinobenzoyl chloride in substantially the same manner as in Working Example 3.

TABLE 2

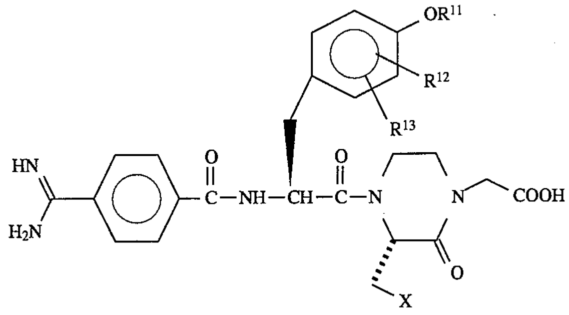

| W. E. No. | $R^{11}$ | $R^{12}$ | $R^{13}$ | X | mp (°C.) | Specific rotation $[a]_D^{20}$ | Rational Formula | Elemental Analysis Calcd. (Found) C | H | N |
|---|---|---|---|---|---|---|---|---|---|---|
| 4 | $C_2H_5$ | H | H | $COOCH_3$ | 212–215 | −78.8° (c = 1.0, DMSO) | $C_{28}H_{33}N_5O_8$ $.3.0H_2O$ | 54.10 (53.85) | 6.32 (6.22) | 11.27 (11.09) |
| 5 | n-$C_3H_7$ | H | H | $COOCH_3$ | 204–208 | −78.7° (c = 1.005, DMSO) | $C_{29}H_{35}N_5O_8$ $3.0H_2O$ | 54.80 (55.06) | 6.50 (6.66) | 11.02 (11.17) |
| 6 | i-$C_3H_7$ | H | H | $COOCH_3$ | 217–220 | −80.2° (c = 0.995, DMSO) | $C_{29}H_{35}N_5O_8$ $.2.0H_2O$ | 56.39 (56.45) | 6.36 (6.24) | 11.34 (11.43) |
| 7 | n-$C_4H_9$ | H | H | $COOCH_3$ | 205-209 | −76.5° (c = 0.96, DMSO) | $C_{30}H_{37}N_5O_8$ $.2.5H_2O$ | 56.24 (56.33) | 6.61 (6.69) | 10.93 (10.92) |
| 8 | $CH_3$ | 3-$OCH_3$ | H | $COOCH_3$ | Powder | −51.2° (c = 1.005, DMSO) | $C_{28}H_{33}N_5O_9$ $.1.5H_2O$ | 55.08 (54.92) | 5.04 (6.10) | 11.47 (11.46) |
| 9 | $C_2H_5$ | 3-$OC_2H_5$ | H | $COOCH_3$ | Powder | −60.9° (c = 1.0, DMSO) | $C_{30}H_{37}N_5O_9$ $.3.5H_2O$ | 53.41 (53.49) | 6.57 (6.43) | 10.38 (10.36) |

TABLE 3

| W.E. No. | $R^{11}$ | $R^{12}$ | $R^{13}$ | X | mp (°C.) | Specific rotation $[a]_D^{20}$ | Rational Formula | Elemental Analysis Calcd. (Found) C | H | N |
|---|---|---|---|---|---|---|---|---|---|---|
| 10 | H | H | H | OH | 235-241 | −80.5° (c = 0.99, DMSO) | $C_{24}H_{27}N_5O_7$ $.2.0H_2O$ | 54.03 (53.78) | 5.86 (6.19) | 13.13 (13.21) |
| 11 | H | H | H | 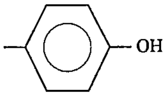 | 243-245 | +38.9° (c = 1.005, 1NHCl) | $C_{30}H_{31}N_5O_7$ $.2.5H_2O$ | 58.25 (58.52) | 5.87 (5.79) | 11.32 (11.54) |

The following compounds of Reference Examples 15–20 were obtained as a colorless oily substance in the same manner as Reference Example 5.

TABLE 4

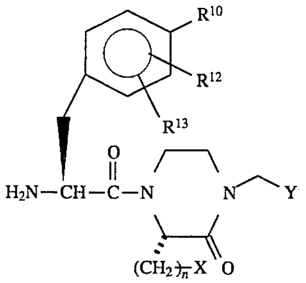

| R. Ex. No. | $R^{10}$ | $R^{12}$ | $R^{13}$ | n | X | Y |
|---|---|---|---|---|---|---|
| 15 | O-i-$C_4H_9$ | H | H | 1 | $COOCH_3$ | $COO^tBU$ |
| 16 | O-sec-$C_4H_9$ | H | H | 1 | $COOCH_3$ | $COO^tBU$ |
| 17 | $OCH_2O(CH_2)_2OCH_3$ | H | H | 1 | $COOCH_3$ | $COO^tBU$ |
| 18 | $OCOCH_3$ | H | H | 1 | $COOCH_3$ | $COO^tBU$ |
| 19 | $OCONHCH_3$ | H | H | 1 | $COOCH_3$ | $COO^tBU$ |
| 20 | $OSO_2CH_3$ | H | H | 1 | $COOCH_3$ | $COO^tBU$ |

The following compounds of Reference Examples 21–26 were obtained as a colorless oily substance in the same manner as Reference Example 10.

TABLE 5

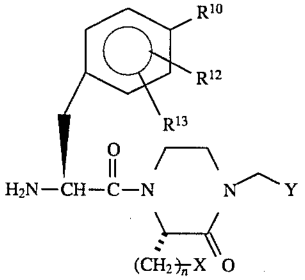

| R. Ex. No. | $R^{10}$ | $R^{12}$ | $R^{13}$ | n | X | Y |
|---|---|---|---|---|---|---|
| 21 | $OCH_2CH{=}CH_2$ | H | H | 1 | $COOCH_3$ | COOH |
| 22 | $OCH_2C{\equiv}CH$ | H | H | 1 | $COOCH_3$ | COOH |
| 23 | $NO_2$ | H | H | 1 | $COOCH_3$ | COOH |
| 24 | F | H | H | 1 | $COOCH_3$ | COOH |

TABLE 5-continued

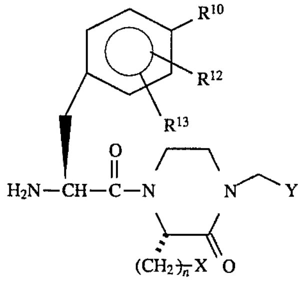

| R. Ex. No. | $R^{10}$ | $R^{12}$ | $R^{13}$ | n | X | Y |
|---|---|---|---|---|---|---|
| 25 | OH | 3-F | H | 1 | $COOCH_3$ | COOH |
| 26 | OH | H | 2-F | 1 | $COOCH_3$ | COOH |

The following compounds of Examples 12–17 were obtained by following the same procedure as that of Example 2 with the use of 4-amidinobenzoyl chloride and the compounds of Reference Examples 15–20, respectively.

TABLE 6

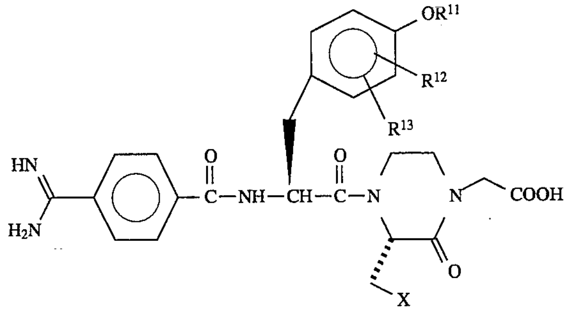

| Working Example No. | $R^{11}$ | $R^{12}$ | $R^{13}$ | X | mp (°C.) | Specific rotation $[a]_D^{20}$ | Rational Formula | Elemental Analysis Calcd. (Found) C | H | N |
|---|---|---|---|---|---|---|---|---|---|---|
| 12 | i-$C_4H_9$ | H | H | $COOCH_3$ | Powder | +75.9°<br>(c = 0.9, $H_2O$) | $C_{30}H_{37}N_5O_8$<br>.HCl.2.5$H_2O$ | 53.21<br>(53.34) | 6.40<br>(6.23) | 10.34<br>(10.50) |
| 13 | sec-$C_4H_9$ | H | H | $COOCH_3$ | Powder | +75.9°<br>(c = 0.9, $H_2O$) | $C_{30}H_{37}N_5O_8$<br>.HCl.2$H_2O$ | 53.93<br>(53.91) | 6.34<br>(6.41) | 10.48<br>(10.74) |
| 14 | $CH_2O(CH_2)_2OCH_3$ | H | H | $COOCH_3$ | Powder | +58.5°<br>(c = 0.5, $H_2O$) | $C_{29}H_{35}N_5O_9$<br>.2$H_2O$ | 54.97<br>(54.79) | 6.20<br>(6.11) | 11.05<br>(11.08) |
| 15 | $COCH_3$ | H | H | $COOCH_3$ | Powder | −99.6°<br>(c = 0.5, DMSO) | $C_{28}H_{31}N_5O_9$<br>.2.5$H_2O$ | 53.67<br>(53.54) | 5.79<br>(5.53) | 11.18<br>(11.10) |
| 16 | $CONHCH_3$ | H | H | $COOCH_3$ | Powder | +56.8°<br>(c = 0.5, $H_2O$) | $C_{28}H_{32}N_6O_9$<br>.3.5$H_2O$ | 50.98<br>(51.00) | 5.96<br>(5.58) | 12.74<br>(12.68) |
| 17 | $SO_2CH_3$ | H | H | $COOCH_3$ | Powder | +49.1°<br>(c = 0.6, $H_2O$) | $C_{27}H_{31}N_5O_{10}S$<br>.2$H_2O$ | 49.61<br>(49.44) | 5.40<br>(5.47) | 10.71<br>(10.71) |

The following compounds of Examples 18–23 were obtained by following the same procedure as that of Example 2 with the use of 4-amidinobenzoyl chloride and the compounds of Reference Examples 21–26, respectively.

TABLE 7

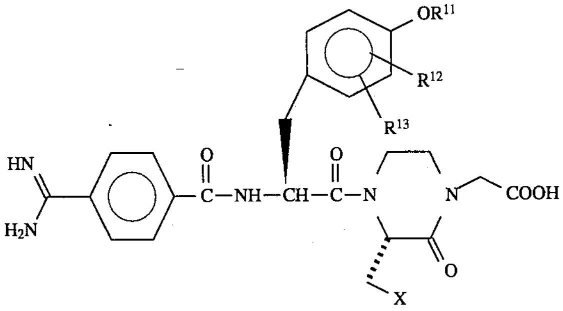

| Working Example No. | $R^{10}$ | $R^{12}$ | $R^{13}$ | X | mp (°C.) | Specific rotation $[a]_D^{20}$ | Rational Formula | Elemental Analysis Calcd. (Found) C | H | N |
|---|---|---|---|---|---|---|---|---|---|---|
| 18 | $OCH_2CH{=}CH_2$ | H | H | $COOCH_3$ | 200–205 | −84.1°<br>(C = 0.8, DMSO) | $C_{29}H_{33}N_5O_8$<br>.1.5$H_2O$ | 57.42<br>(57.52) | 5.98<br>(5.87) | 11.54<br>(11.56) |
| 19 | $OCH_2C{\equiv}CH$ | H | H | $COOCH_3$ | Powder | +78.0°<br>(C = 1.0, $H_2O$) | $C_{29}H_{33}N_5O_8$<br>.HCl.2$H_2O$ | 53.58<br>(53.35) | 5.58<br>(5.37) | 10.77<br>(10.77) |
| 20 | $NO_2$ | H | H | $COOCH_3$ | 218–222 | −146.7°<br>(C = 1.0, DMSO) | $C_{26}H_{28}N_6O_9$<br>.4$H_2O$ | 48.75<br>(48.75) | 5.66<br>(5.29) | 13.12<br>(13.12) |
| 21 | F | H | H | $COOCH_3$ | Powder | +55.2°<br>(C = 0.4, $H_2O$) | $C_{26}H_{28}FN_5O_7$<br>.2$H_2O$ | 54.07<br>(54.40) | 5.58<br>(5.60) | 12.13<br>(12.33) |
| 22 | OH | 3-F | H | $COOCH_3$ | Powder | −112.0°<br>(C = 0.4, DMSO) | $C_{26}H_{28}FN_5O_8$<br>.3$H_2O$ | 51.06<br>(51.30) | 5.60<br>(5.56) | 11.45<br>(11.43) |
| 23 | OH | H | 2-F | $COOCH_3$ | Powder | −116.0°<br>(C = 0.4, DMSO) | $C_{26}H_{28}FN_5O_8$<br>.1.5$H_2O$ | 53.42<br>(53.49) | 5.35<br>(5.57) | 11.98<br>(12.05) |

EXAMPLE 24

(S)-4-{4-Amidinobenzoyl-(3,4-dihydroxy)-DL-phenylalanyl}-3-Methoxycarbonyl-2-Oxopiperazine-1Acetic Acid Using (S)-3-methoxycarbonylmethyl-2-oxopiperazine-acetic acid tert-butyl ester oxalic acid salt obtained in Reference Example 2, N-benzyloxycarbonyl-3,4-di (methoxymethyloxy)-DL-phenylalanine and 4-amidinobenzoyl-chloride, substantially the same procedures as in Reference Example 5 and Example 3 were taken to give the title compound as a colorless amorphous powdery product.

Specific rotation $[\alpha]_D^{20}$ 64.2° (C=0.5, $H_2O$)

Elemental Analysis: $C_{26}H_{29}N_5O_9.2H_2O$

Calcd.: C, 52.79; H, 5.62; N, 11.84

Found: C, 52.83; H, 5.75; N, 11.66

EXAMPLE 25

(S)-4-{4 -Amidinobenzoyl-(4-Chloro)-DL-Phenylalanyl}-3-Methoxycarbonyl-2-Oxopiperazine-1-Acetic Acid Using (S)-3-methoxycarbonylmethyl 2-oxopiperazine-1-acetic acid tert-butyl ester oxalic acid salt obtained in Reference Example 2, N-benzyloxycarbonyl-4-chloro-DL-phenylalanine and 4-amidinobenzoylchloride, substantially the same procedures as in Reference Example 10 and Example 2 were taken to give the title compound as a colorless amorphous powdery product.

Specific rotation $[\alpha]_D^{20}$ 56.8° (C=0.45, $H_2O$)

Elemental Analysis: $C_{26}H_{28}ClN_5O_7.H_2O$

Calcd.: C, 54.22; H, 5.25; N, 12.16

Found: C, 53.98; H, 5.31; N, 12.33

REFERENCE EXAMPLE 27

Ethyl N-$^t$Butoxycarbonyl-L-Tyrosinate

In a mixture of 125.0 ml of water and 125.0 ml of 1,4-dioxane were dissolved 25.0 g of ethyl L-tyrosinate hydrochloride and 9.41 g of sodium hydrogencarbonate. To the solution was added, while stirring at room temperature, 25.7 ml of di-$^t$butyl dicarbonate. The mixture was stirred for one hour, which was shaken with methylene chloride for extraction. The organic layer was concentrated under reduced pressure. The residue was dissolved in a small volume of ethyl acetate, to which petroleum ether was added to cause crystallization. m.p.: 83°–86°

Specific rotation $[\alpha]_D^{20}$41.7° (C=1.0, $CHCl_3$)

Elemental Analysis: $C_{16}H_{22}NO_5.0.1H_2O$

Calcd.: C, 61.96; H, 7.21; N, 4.52

Found: C, 61.81; H, 7.41; N, 4.51

REFERENCE EXAMPLE 28

Ethyl N-$^t$Butoxycarbonyl-4-Trifluoromethanesulfonyloxy-L-Phenyl Alanate

In 97.3 ml of methylene chloride were dissolved 6.0 g of ethyl N-$^t$butoxycarbonyl-L-tyrosinate, 3.40 ml of 2,6-lutidine and 0.48 g of 4-dimethylaminopyridine. To the solution was added dropwise gradually, while stirring at −30° C., 4.91 ml of trifluoromethanesulfonic acid anhydride followed by stirring for one hour at room temperature. To the reaction solution was added water, which was shaken with methylene chloride for extraction. The organic layer was concentrated under reduced pressure. The concentrate was roughly purified by means of a silica gel column chromatography (hexane/ethyl acetate=4/1), which was crystallized from (ethyl acetate/pentane) to give 4.9 g (57.2%) of the title compound as pale reddish crystals. m.p.: 49°–50° C.

Specific rotation $[\alpha]_D^{20}$+32.3° C. (C=1.0, $CHCl_3$)

Elemental Analysis: $C_{17}H_{21}F_3NO_7S$

Calcd.: C, 46.36; H, 4.81; N, 3.18

Found: C, 46.52; H, 5.07; N, 3.13

REFERENCE EXAMPLE 29

Ethyl N-$^t$Butoxycarbonyl-4-Vinyl-L-Phenylalanate

In 49.1 ml of N,N-dimethylformamide were dissolved 2.89 g of ethyl N-$^t$butoxycarbonyl-4-trifluoromethanesulfonyloxy-L-phenyl alanate, 834 mg of lithium chloride, 92.1 mg of bis(triphenylphosphine)palladium (II) chloride, 145 mg of 2,6-di-$^t$butyl-4-methylphenol and 1.99 ml of vinyl tributyltin. The solution was stirred for 2 hours at 90° C. under nitrogen atmosphere. To the reaction solution were added 3.31 ml of pyridine and 6.61 ml of pyridinium fluoride (a 1.4M tetrahydrofuran solution). The mixture was further stirred for 18 hours at room temperature. To the reaction solution was added water, then insolubles were filtered off. The filtrate was shaken with ethyl acetate for extraction. The organic layer was concentrated under reduced pressure. The concentrate was purified by means of a silica gel chromatography (hexane/ethyl acetate=4/1) to give 1.65 g (78.5%) of the title compound as a pale yellow oily product.

IRνmax $cm^{-1}$: 2978, 2932, 1738, 1713, 1510, 1444, 1390, 1366, 1346, 1249, 1168, 1095, 1056, 989, 906, 850, 828, 777

NMR($CDCl_3$)δ: 1.24(t,J=7.2 Hz,3H), 1.42(s,9H), 2.90–3.21(m,2H), 4.17(q,J=7.2 Hz,2H), 4.47–4.63(m, 1H), 4.90–5.08(m,1H), 5.23(d,J=10.8 Hz,1H), 5.72(d,J=17.6 Hz,1H), 6.69(dd,J=17.6 Hz,J=11.0 Hz,1H), 7.10(d, J=8.0 Hz,2H), 7.34(d,J=8.2 Hz,2H)

REFERENCE EXAMPLE 30

N-$^t$Butoxycarbonyl-4-Vinyl-L-Phenylalanine

In 5.17 ml of a mixture solvent of methanol: water=10:1 was dissolved 1.65 g of ethyl N-$^t$butoxycarbonyl-4-vinyl-L-phenylalanate and 0.24 g of lithium hydroxide monohydrate. The solution was stirred for 20 minutes at room temperature. The reaction solution was adjusted to pH 2–3 with 1N HCl, which was shaken with ethyl acetate for extraction, The organic layer was concentrated under reduced pressure to give 1.40 g (92,7%) of the title compound as a colorless oily product compound.

IRνmax $cm^{-1}$: 3428, 2978, 1714, 1511, 1442, 1393, 1366, 1249, 1164, 1055

NMR($CDCl_3$)δ: 1.42(s,9H), 2.99–3.28(m,2H), 4.53–4.70(m,1H), 4.83–5.04(m,1H), 5.23(d,J=10.8 Hz,1H), 5.73(d,J=17.6 Hz,1H), 6.69(dd,J=11.0 Hz,J=17.6 Hz,1H), 6.40–7.00(br,1H), 7.14(d,J=8.2 Hz,2H), 7.35(d, J=8.2 Hz,2H)

REFERENCE EXAMPLE 31

(S)-4-(N-$^t$Butoxycarbonyl-4-Vinyl-L-Phenylalanyl)-3-Methoxycarbonylmethyl-2-Oxopiperazine-1-Acetic Acid $^t$Butyl Ester In 21.7 ml of methylene chloride were dissolved 2.17 g of (S)-3-methoxycarbonylmethyl-2-oxopiperazine-1-acetic acid ${}^t$butyl ester oxalic acid salt and 1.40 g of N-${}^t$butoxycarbonyl-4-vinyl-L-phenylalanine. To the solution was added gradually, while cooling with water, 1.38 g of 1-ethyl-3-(3-dimethylaminopropyl)carbodiimide hydrochloride, over 5 minutes. The mixture was stirred for one hour at room temperature, then methylene chloride was distilled off under reduced pressure. The residue was dissolved in ethyl acetate, which was washed with a 5% aqueous solution of potassium hydrogensulfate and a saturated aqueous solution of sodium hydrogencarbonate. The organic layer was dried over anhydrous magnesium sulfate. The residue was crystallized with (ethyl acetate/petroleum ether) to give 2.04 g (75.8%) of the title compound as a while crystalline product. m.p.: 148°–152° C.

Specific rotation $[\alpha]_D^{20}$+94.3° C. (C=0.5%, $CHCl_3$)

Elemental Analysis: $C_{29}H_{41}N_3O_8$

Calcd.: C, 62.24; H, 7.38; N, 7.51

Found: C, 62.01; H, 7.51; N, 7.47

EXAMPLE 26

(S)-4-(4-Amidinobenzoyl-L-4-Vinylphenylalanyl)-3-Methoxycarbonylmethyl-2-Oxopiperazine-1-Acetic Acid In a mixture of 3.0 ml of methylene chloride and 3.0 ml of trifluoroacetic acid was dissolved 0.60 g of (S)-4-(N-${}^t$butoxycarbonyl-4-vinyl-L-phenylalanyl)-3-methoxycarbonylmethyl-2-oxopiperazine-1-acetic acid ${}^t$butyl ester. The solution was stirred for one hour at room temperature. The reaction solution was concentrated under reduced pressure. The residue was subjected to azeotropy with toluene several times. This product was dissolved in a mixture of 11.1 ml of $H_2O$ and 5.6 ml of 1,4-dioxane. To the solution was added 0.45 g of sodium hydrogencarbonate at room temperature, followed by addition of 0.35 g of 4-amidinobenzoyl chloride at room temperature, over 5 minutes. The mixture was stirred for one hour, which was adjusted to pH 2–3 with 1N HCl . The reaction mixture was concentrated under reduced pressure. The residue was purified by means of a CHP-20 column ($H_2O$→5% $CH_3CN/H_2O$→10% $CH_3CN/H_2O$→15% $CH_3CN/H_2O$→20% $CH_3CN/H_2O$), which was converted to corresponding hydrochloride with 1N HCl, followed by lyophilization to give 0.39 g (58.4%) of the title compound as a colorless amorphous powdery product.

Specific rotation $[\alpha]_D^{20}$+84.9° C. (C=1.0%, $H_2O$)

Elemental Analysis: $C_{28}H_{32}N_5O_7Cl.2.0H_2O$

Calcd.: C, 54.06; H, 5.83; N, 11.26

Found: C, 53.82; H, 5.52; N, 11.11

Example 27

(S)-4-(4-Amidinobenzoyl-L-4-Ethynylphenylalanyl)-3-Methoxycarbonylmethyl-2-Oxopiperazine-1-Acetic Acid In 50.5 ml of dimethylformamide were dissolved 2.97 g of ethyl N-${}^t$butoxycarbonyl-4-trifluoromethanesulfonyloxy-L-phenylalanate, 857 mg of lithium chloride, 94.6 mg of bis(triphenylphosphine)palladium (II) chloride, 149 mg of 2,6-di-${}^t$butyl-4-methylphenol and 2.03 ml of ethynyl tributyltin. The solution was stirred for 2 hours at 90° C. under nitrogen atmosphere. To the reaction system were added 4.8 ml of pyridine and 9.6 ml of pyridinium fluoride (a 1.4M tetrahydrofuran solution). The mixture was stirred for further 18 hours at room temperature. To the reaction solution was added water, and insolubles were filtered off. The filtrate was shaken with ethyl acetate for extraction, and the organic layer was concentrated under reduced pressure. The concentrate was purified by means of silica gel column chromatography (hexane/ethyl acetate=4/1). This product and 34.3 mg of lithium hydroxide monohydrate were dissolved in 0.74 ml of a mixture solvent of methanol: water=10:1, followed by stirring for 45 minutes at room temperature. The reaction system was adjusted to pH 2–3 with 1H HCl water, which was shaken with ethyl acetate for extraction. The organic layer was concentrated under reduced pressure to give N-${}^t$butoxycarbonyl-4-ethynyl-L-phenylalanine as a colorless oily product. This product and 0.42 g of (S)-3-methoxycarbonylmethyl-2-oxopiperazine-1-acetic acid ${}^t$butyl ester oxalic acid salt were dissolved in 4.2 ml of methylene chloride. To the solution was added gradually, while cooling with water, 0.24 g of 1-ethyl-3-(3-dimethylaminopropyl)carbodiimide hydrochloride, over 5 minutes. The mixture was stirred for one hour at room temperature. Methylene chloride was distilled off under reduced pressure. The residue was dissolved in ethyl acetate, and the solution was washed with a 5% aqueous solution of potassium hydrogensulfate and a saturated sodium hydrogencarbonate. The organic layer was dried over anhydrous magnesium sulfate, which was then concentrated under reduced pressure. The residue was purified by means of a silica gel chromatography (hexane/ethyl acetate=2/3) to give 370 mg of (S)4-(N-${}^t$butoxycarbonyl-4-ethynyl-L-phenylalanyl)-3-methoxycarbonylmethyl-2-oxopiperazine-1-acetic acid ${}^t$butyl ester as a colorless oily product. This product was dissolved in a mixture of 1.9 ml of methylene chloride and 1.9 ml of trifluoroaaetic acid. The solution was stirred for one hour at room temperature. The reaction solution was concentrated under reduced pressure, which was subjected to azeotropy with toluene several times. The residue was dissolved in a mixture of 6.8 ml of $H_2O$ and 3.4 ml of 1,4-dioxane. To the solution was added 0.28 g of sodium hydrogencarbonate, to which was then added 0.22 g of 4-amidinobenzoylchloride at room temperature, over 5 minutes. The mixture was stirred for one hour, which was adjusted to pH 2–3 with 1N HCl. The reaction mixture was concentrated under reduced pressure. The residue was purified by means of a CHP-20 column ($H_2O$→5% $CH_3CN/H_2O$→10% $CH_3CN/H_2O$→15% $CH_3CN/H_2O$→20% $CH_3CN/H_2O$), which was converted into the corresponding hydrochloride with 1N HCl water, followed by lyophilization to give 0.13 g (3.0%) of the title compound as a colorless amorphous powdery product.

Specific rotation $[\alpha]_D^{20}$+57.2° C. (C=1.0, $H_2O$)

Elemental Analysis: $C_{28}H_{30}N_5O_7Cl.3.0H_2O$

Calcd.: C, 52.71; H, 5.69; N, 10.98

Found: C, 52.61; H, 5.51; N, 11.06

REFERENCE EXAMPLE 32

${}^t$Butyl N-Benzyloxycarbonyl-L-Tyrosinate

In a mixture of 25.0 ml of $H_2O$ and 25.0 ml of 1,4-dioxane were dissolved 5.0 g of ${}^t$butyl L-tyrosinate and 2.65 g of sodium hydrogencarbonate. To the solution was added 4.51 ml of benzyloxycarbonyl chloride while stirring at room temperature. The mixture was stirred for 15 minutes, followed by shaking with ethyl acetate for extraction. The organic layer was concentrated under reduced pressure. The concentrate was purified by means of a silica gel chromatography (hexane/ethyl acetate=2/1) to give 7.79 g of the title compound as a pale yellow oily product.

IRvmax $cm^{-1}$ : 3346, 2978, 1700, 1613, 1594, 1514, 1452, 1366, 1227, 1153, 1103, 1057, 842, 751, 696

NMR($CDCl_3$)δ: 1.41(s,9H), 2.83–3.10(m,2H), 4.48(dd,J=6.2 Hz,J=14.4 Hz,1H), 5.08(s,2H), 5.31(d,J=8.2 Hz,1H), 6.22(s,1H), 6.69(d,J=8.4 Hz,2H), 6.97(d,J=8.4 Hz,2H), 7.32(s,5H)

REFERENCE EXAMPLE 33

ᵗButyl N-Benzyloxycarbonyl-4-Trifluoromethanesulfonyloxy-L-Phenylalanate

In 210 ml of methylene chloride were dissolved 15.6 g of ᵗbutyl N-benzyloxycarbonyl-L-tyrosinate, 7.36 ml of 2,6-llutidine and 1.03 g of 4-dimethyl aminopyridine. To the solution was added dropwise gradually, while stirring at −30° C., 10.6 ml of trifluoromethanesulfonic acid anhydride, followed by stirring the mixture for one hour at room temperature. To the reaction mixture was added water, and the mixture was shaken with methylene chloride for extraction. The organic layer was concentrated under reduced pressure. The concentrate was purified by means of a silica gel chromatography (hexane/ethyl acetate=4/1) to give 11.39 g (53.7%) of the title compound.

IRvmax $cm^{-1}$ : 3380, 1741, 1697, 1530, 1501, 1419, 1369, 1348, 1249, 1226, 1143, 1058, 1016, 892, 712, 696, 608, 498 NMR($CDCl_3$)δ: 1.37(s,9H), 3.10(d,J=6.2 Hz,2H), 4.52(dd,J=6.4 Hz,J=14.0 Hz,1H), 5.09(dd,J=12.2 Hz,J=14.0 Hz,2H), 5.31(d,J=7.8 Hz,1H), 7.10–7.28(m,4H), 7.35(s,5H)

REFERENCE EXAMPLE 34

ᵗButyl N-benzyloxycarbonyl-4-Methoxycarbonyl-L-Phenylalanate

In a mixture of 15.0 ml of methanol and 20.0 ml of dimethyl sulfoxide were dissolved 2.0 g of ᵗbutyl N-benzyloxycarbonyl-4-trifluoromethanesulfonyloxy-L-phenylalanate, 164 mg of 1,3-bis (diphenylphosphino)propane, 89.1 mg of palladium(II)acetate and 1.11 ml of triethylamine. Into the mixture was introduced for 5 minutes carbon monoxide by bubbling. The mixture was further stirred for 2 hours at 80° C. under carbon monoxide atmosphere. To the reaction mixture was added water, which was shaken with ethyl acetate for extraction. The organic layer was concentrated under reduced pressure. The residue was purified by means of a silica gel chromatography (hexane/ethyl acetate=3/1) to give 1.52 g (92.7%) of the title compound as a colorless oily product.

IRvmax cm–1: 3346, 2978, 2950, 1720, 1610, 1515, 1452, 1434, 1367, 1351, 1279, 1220, 1178, 1154, 1107, 1056, 1020, 844, 751, 697

NMR($CDCl_3$)δ: 1.39(s,9H), 3.00–3.25(m,2H), 3.90(s,3H), 4.56(dd,J=7.0 Hz,J=13.0 Hz,1H), 5.09(dd,J=15.2 Hz,J=17.0 Hz,2H), 5.32(d,J=8.0 Hz,1H), 7.23(d,J=9.0 Hz,2H), 7.34(s,5H), 7.94(d,J=8.0 Hz,2H)

REFERENCE EXAMPLE 35

N-Benzyloxycarbonyl-4-Methoxycarbonyl-L-Phenylalanine

In a mixture of 2.75 ml each of trifluoroacetic acid and methylene chloride was dissolved 0.55 g of ᵗbutyl N-benzyloxycarbonyl-4-methoxycarbonyl-L-phenylalanate. The solution was stirred for 1.5 hour at room temperature. The reaction mixture was concentrated under reduced pressure, and the concentrate was subjected to azeotropy several times with toluene. The residue was dissolved in a small volume of ethyl acetate, which was crystallized from petroleum ether to give 469 mg (98.7 %) of the title compound as a white crystalline product.

Specific rotation $[\alpha]_D^{20}$+58.6° C. (C=0.1, $CHCl_3$) m.p.: 102°–106° C.

Elemental Analysis: $C_{19}H_{19}NO_6$

Calcd.: C, 63.89; H, 5.36; N, 3.92

Found: C, 63.70; H, 5.47; N, 3.95

REFERENCE EXAMPLE 36

(S)-4-(N-Benzyloxycarbonyl-4-Methoxycarbonyl-L-Phenylalanyl)-3-Methoxycarbonylmethyl-2-Oxopiperazine-1-Acetic Acid ᵗButyl Ester In 7.6 ml of methylene chloride were dissolved 0.76 g of (S)-3-methoxycarbonylmethyl-2-oxopiperazine-1-acetic acid ᵗbutyl ester oxalic acid salt and 0.47 g of N-benzyloxycarbonyl-4-methoxycarbonyl-L-phenylalanine. To the solution was added gradually, while cooling with water, 0.44 g of 1-ethyl-3-(3-dimethylaminopropyl) carbodiimide, over 5 minutes. The mixture was stirred for one hour at room temperature, then methylene chloride was distilled off under reduced pressure. The residue was dissolved in ethyl acetate. The solution was washed with a 5% aqueous solution of potassium hydrogensulfate and a saturated aqueous solution of hydrogencarbonate. The organic layer was dried over anhydrous magnesium sulfate, followed by concentration under reduced pressure. The residue was purified by means of a silica gel chromatography (hexane/ethyl acetate=l/2) to give 0.46 g (51.1%) of the title compound as a colorless oily product.

IRvmax $cm^{-1}$ : 3322, 2980, 2952, 1719, 1649, 1525, 1489, 1435, 1367, 1281, 1152, 1104, 1020, 978, 846, 748, 699

NMR($CDCl_3$)δ: 1.45(s,9H), 2.61–2.72(m, 1H), 2.72–3.25(m,5H), 3.63(s,3H), 3.40–4.05(m,4H), 3.90(s, 3H), 4.78–5.20(m,4H), 5.61(d,J=8.0 Hz,1H), 7.16–7.46(m,7H), 7.95(d,J=8.0 Hz,2H)

EXAMPLE 28

(S)-4-(4-Amidinobenzoyl-L-4-Methoxycarbonylphenylalanyl)-3-Methoxycarbonylmethyl-2-Oxopiperazine-1-Acetic Acid In 4.6 ml of ethyl acetate was dissolved 0.46 g of (S)-4-(N-benzyloxycarbonyl-4-methoxycarbonyl-L-phenylalanyl)-3-methoxycarbonylmethyl-2-oxopiperazine-1-acetic acid ᵗbutyl ester. To the solution was added 0.19 g of 10% palladium-carbon, which was stirred for 3 hours under hydrogen atmosphere. The catalyst was filtered off, and the filtrate was concentrated to give a colorless oily product. This product was dissolved in 3.0 ml of methylene chloride and 3.0 ml of trifluoroacetic acid. The mixture was stirred for one hour at room temperature. The reaction mixture was concentrated under reduced pressure. The concentrate was subjected to azeotropy several times with toluene. This product was dissolved in a mixture of 8.1 ml of water and 4.0 ml of 1,4-dioxane. To the solution was added, at room temperature, 0.31 g of sodium hydrogencarbonate, followed by addition of 0.24 g of 4-amidinobenzoylchloride at room temperature, over 5 minutes. The mixture was stirred for one hour, whose pH was adjusted to 2–3 with 1N HCl. The reaction mixture was then concentrated under reduced pressure. The concentrate was purified by means of a CHP-20 column ($H_2O$→5% $CH_3CN/H_2O$→10% $CH_3CN/H_2O$→15% $CH_3CN/H_2O$→20% $CH_3CN/H_2O$). Further, the product was converted into its hydrochloride with 1N HCl water, followed by lyophilization to afford 0.26 g (53.0%) of the title compound as a colorless amorphous powdery product.

Specific rotation $[\alpha]_D^{20}$+57.1° C. (C=1.0%, $H_2O$)

Elemental Analysis: $C_{28}H_{32}N_5O_9.2.5H_2O$

Calcd.: C, 50.72; H, 5.62; N, 10.56

Found: C, 50.68; H, 5.50; N, 10.48

REFERENCE EXAMPLE 37

(S)-4-(N-$^t$Butoxycarbonyl-4-Formyl-L-Phenylalanyl)-3-Methoxycarbonylmethyl-2-Oxopiperazine-1-Acetic Acid $^t$Butyl Ester In a mixture of 22.1 ml of carbon tetrachloride, 22.1 ml of acetonitrile and 33.2 ml of water were dissolved 2.21 g of (S)-4-(N-$^t$butoxycarbonyl-4-vinyl-L-phenylalanyl)-3-methoxycarbonylmethyl-2-oxopiperazine-1-acetic acid $^t$butyl ester and 3.46 g of sodium metaperiodate. To the solution was added 16.4 mg of ruthenium (III) chloride n hydrate at room temperature. The mixture was stirred for one hour. The reaction mixture was shaken with ethyl acetate for extraction. The organic layer was concentrated under reduced pressure. The residue was purified by means of a silica gel chromatography (hexane/ethyl acetate=1/2) to give 1.14 g (51.4%) of the title compound as a colorless oily product.

IRvmax $cm^{-1}$: 2978, 2934, 1740, 1702, 1654, 1605, 1489, 1436, 1366, 1247, 1228, 1157, 1047, 1016, 979, 848

NMR($CDCl_3$)δ: 1.40(s,9H), 1.45(s,9H), 2.66–3.27(m,6H), 3.42–3.93(m,6H), 4.05–4.36(m, 1H), 4.72–4.90(m, 1H), 4.98(t,J=5.0 Hz,1H), 5.35(d,J=9.0 Hz,1H), 7.34–7.60(m, 2H), 7.83(d,J=8.0 Hz,2H), 9.98(s,1H)

EXAMPLE 29

(S)-4-(4-Amidinobenzoyl-L-4-Formylphenylalanyl)-3-Methoxycarbonylmethyl-2-Oxopiperazine-1-Acetic Acid In a mixture of 1.1 ml of methylene chloride and 1.1 ml of trifluoroacetic acid was dissolved 0.22 g of (S)-4-(N-$^t$butoxycarbonyl-4-formyl-L-phenylalanyl)-3-methoxycarbonylmethyl-2-oxopiperazine-1-acetic acid $^t$butyl ester. The solution was stirred for one hour at room temperature. The reaction solution was concentrated under reduced pressure, and the residue was subjected to azeotropy several times with toluene. The product was dissolved in a mixture of 4.1 ml of water and 2.0 ml of 1,4-dioxane. To the solution was added 0.16 g of sodium hydrogencarbonate at room temperature. To the mixture was then added 0.13 g of 4-amidinobenzoyl chloride at room temperature over 5 minutes. The mixture was stirred for one hour, whose pH was adjusted to 2–3 with 1N HCl. The reaction mixture was concentrated under reduced pressure. The residue was purified by means of a CHP-20 column ($H_2O$→5% $CH_3CN/H_2O$→10% $CH_3CN/H_2O$→15% $CH_3CN/H_2O$) to give 0.15 g (64.9%) of the title compound as a white lyophilized product.

Specific rotation $[\alpha]_D^{20}$+28.6° C. (C=1.0, $H_2O$)

Elemental Analysis: $C_{27}H_{29}N_5O_8.3.0H_2O$

Calcd.: C, 53.55; H, 5.83; N, 11.56

Found: C, 53.61; H, 5.74; N, 11.68

REFERENCE EXAMPLE 38

(S)-4-(N-$^t$Butoxycarbonyl-4-Hydroxymethyl-L-Phenylalanyl)-3-Methoxycarbonylmethyl-2-Oxopiperazine-1-Acetic Acid $^t$Butyl Ester In 13.0 ml of methanol was dissolved 0.65 g of (S)-4-(N-$^t$butoxycarbonyl-4-formyl-L-phenylalanyl)-3-methoxycarbonylmethyl- 2-oxopiperazine-1-acetic acid $^t$butyl ester. To the solution was added 21.9 mg of sodium borohydride while stirring at 0° C. The mixture was stirred for one hour at room temperature. To the reaction mixture was added water, which was shaken with methylene chloride for extraction. The organic layer was concentrated under reduced pressure. The residue was purified by means of a silica gel chromatography (methylene chloride/ethyl acetate=2/3) to give 0.56 g (85.6%) of the title compound as a colorless oily product.

IRvmax $cm^{31\ 1}$: 3428, 2978, 2932, 1740, 1708, 1647, 1489, 1437, 1366, 1248, 1156, 1048, 1015

NMR($CDCl_3$)δ: 1.44(s,9H), 1.45(s,9H), 2.18–2.40(m, 1H), 2.52–3.25(m,6H), 3.63(s,3H), 3.40–4.02(m,3H), 4.30(d, J=16.0 Hz,1H), 4.63(s,2H), 4.68–4.94(m,2H), 5.23–5.50(m, 1H), 7.10–7.40(m,4H)

EXAMPLE 30

(S)-4-(4-Amidinobenzoyl-L-4-Hydroxymethylphenylalanyl)-3-Methoxycarbonylmethyl-2-Oxopiperazine-1-Acetic Acid In a mixture of 2.0 ml of methylene chloride and 2.0 ml of trifluoroacetic acid was dissolved 0.26 g of (S)-4-(N-$^t$butoxycarbonyl-4-hydroxymethyl-L-phenylalanyl)-3-methoxycarbonylmethyl-2-oxopiperazine-1-acetic acid $^t$butyl ester. The solution was stirred for one hour at room temperature. The reaction mixture was concentrated under reduced pressure, which was subjected to azeotropy several times with toluene. This product was dissolved in a mixture solvent of 4.8 ml of water and 2.4 ml of 1,4-dioxane. To the solution was added 0.19 g of sodium hydrogencarbonate at room temperature, followed by addition of 0.15 g of 4-amidinobenzoylchloride at room temperature over 5 minutes. The mixture was stirred for one hour, whose pH was adjusted to 2–3 with 1N HCl water, followed by concentration under reduced pressure. The concentrate was purified by means of a CHP-20 column ($H_2O$→5% $CH_3CN/H_2O$→10% $CH_2CN/H_2O$) to give 0.17 g (60.7%) of the title compound as a colorless lyophilized product.

Specific rotation $[\alpha]_D^{20}$+62.5° C. (C=1.0, $H_2O$)

Elemental Analysis: $C_{27}H_{31}N_5O_8.3.0H_2O$

Calcd.: C, 53.37; H, 6.14; N, 11.53

Found: C, 53.50, H, 5.94; N, 11.46

EXAMPLE 31

(S)-4-{4-(2-Aminoethyl)Benzoyl-O-Methyl-L-Tyrosyl}-3-Methoxycarbonyl-2-Oxopiperazine-1-Acetic Acid In 5 ml of dichloromethane were dissolved 400 mg of 4-(2-tert-butoxycarbonylaminoethyl)benzoic acid and 203 mg of 1-hydroxybenztriazole monohydrate. To the solution was added, at room temperature, 400 mg of 1-ethyl-3-(3-dimethylaminopropyl)carbodiimide. The mixture was stirred for one hour. To this solution was added 300 mg of triethylamine. To the mixture was added 2 ml of dichloromethane solution of 785 mg of (S)-4-)-O-methyl-L-tyrosyl-3-methoxycarbonylmethyl-2-oxopiperazine-1-acetic acid tert-butyl ester acetic acid salt obtained in Reference Example 5. The mixture was stirred for 2 hours at room temperature. The reaction mixture was diluted with dichloromethane, which was washed with a saturated aqueous solution of sodium hydrogencarbonate and a 5% aqueous solution of potassium hydrogensulfate, followed by drying over magnesium sulfate, followed by concentration under reduced pressure to give a crude product. The crude product was dissolved in mixture of 3 ml of dichloromethane and 3 ml of trifluoroacetic acid. The solution was left standing for one hour at room temperature, followed by concentration under reduced pressure. The residue was purified by means of a MCI GEL CHP20P (Mitsubishi Chemical Industries, Ltd.) (eluent $H_2O \rightarrow 15\%$ $CH_3CN$), followed by lyophilization to afford 490 mg of the title compound as a colorless powdery product.

Specific rotation $[\alpha]_d^{20}$+68.4° C. (C=0.45 $H_2O$)

Elemental Analysis: $C_{28}H_{34}N_4O_8.2H_2O$

Calcd.: C, 56.95; H, 6.48; N, 9.49

Found: C, 56.80; H, 6.61; N, 9.20

REFERENCE EXAMPLE 39

(S)-4-(N-Benzyloxycarbonyl-O-Methyl-L-Tyrosyl)-3-Methoxycarbonylmethyl-2-Oxopiperazine-1-Acetic Acid To a mixture of 28.8 g of (S)-3-methoxycarbonyl-2-oxopiperazine-1-acetic acid $^t$butyl ester, 23.0 g of N-benzyloxycarbonyl-O-methyl-L-tyrosine and 202 ml of methylene chloride, 15.3 g of 1-(3-dimethylaminopropyl)-3-ehtylcarbodiimide was added. The mixture was stirred for 2 hours and concentrated under reduced pressure. The residue was disolved in ethyl acetate. The solution was washed with a 5% aqueous solution of potassium hydrogensulfate and a saturated sodium hydrogen carbonate. The organic layer was concentrated under reduced pressure to give 37.0 g of crude (S)-4-(N-benzyloxycarbonyl-O-methyl-L-tyrosyl)-3-methoxycarbonylmethyl-2-oxopiperazine-1-acetic acid $^t$butyl ester. This product was dissolved in 74.0 ml of methylene chloride, to which was added 74.0 ml of trifluoroacetic acid. The mixture was stirred for one hour at room temperature. The reaction solution was concentrated under reduced pressure. The residue was subjected to azeotropy with toluene several times to afford 39.12 g of the title compound as a colorless oily product.

IRvmax $cm^{-1}$: 3422, 1720, 1643, 1512, 1438, 1299, 1246, 1177, 1027, 980, 823, 740, 696

NMR($CDCl_3$)δ: 2.30–2.90(m,6H), 2.90–3.83(m,7H), 3.71(s,3H), 3.90–4.15(m, 1H), 4.50–4.75(m, 1H), 4.80–4.95(m,1H), 4.96(s,2H), 6.81(d,J=8.6 Hz,2H), 7.10–7.40(m,7H)

REFERENCE EXAMPLE 40

(S)-4-(N-Benzyloxycarbonyl-O-Methyl-L-Tyrosyl)-3-Me-thoxycarbonylmethyl-2-Oxo-Piperazine-1-Acetic Acid Dimethylaminocarbonylmethyl Ester.

In 7.39 ml of N,N-dimethylformamide were dissolved 2.0 g of (S)-4-(N-benzyloxycarbonyl-O-methyl-L-tyrosyl)-3-methoxycarbonylmethyl-2-oxopiperazine-1-acetic acid, 83,0 mg of sodium iodide and 563 μl of N,N-dimethylaminocarbonylmethyl chloride. To the solution was added 772 μl of triethylamine while stirring at room temperature. The mixture was stirred for 6 hours, to which was then added water. The mixture was shaken with ethyl acetate for extraction. The organic layer was concentrated under reduced pressure. The residue was purified by means of a silica gel chromatography (methylene chloride/methanol =13/1) to give 1.57 g (68.0%) of the title compound as a colorless oily product.

IRvmax $cm^{-1}$: 2944, 1738, 1651, 1511, 1437, 1343, 1246, 1202, 1028, 821, 748, 697

NMR($CDCl_3$)δ: 2.47–2.68(m,1H), 2.76–3.23(m,5H), 2.95 (s,3H), 2.96(s,3H), 3.58–3.84(m,2H), 3.63(s,3H), 3.77 (s,3H), 4.04(d,J=17.0 Hz,1H), 4.34(d,J=17.0 Hz,1H), 4.72–4.89(m,3H), 4.92–5.06(m,1H), 5.09(s,2H), 5.54 (d,J=10 Hz,1H), 6.80(d,J=8.4 Hz,2H), 7.08 (d,J=8.4 Hz,2H), 7.36(s,5H)

By substantially the same procedure as in Reference Example 40, the following compounds of Reference Example Nos. 41–43 were obtained as colorless oily products.

TABLE 8

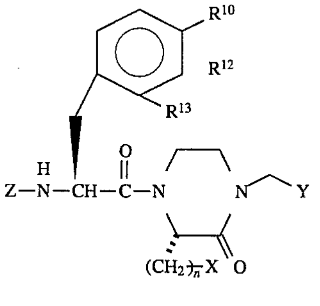

| R. Ex. No. | $R^{10}$ | $R^{12}$ | $R^{13}$ | n | X | Y | $H^1$-NMR ($CDCl_3$: δ) |
|---|---|---|---|---|---|---|---|
| 41 | $OCH_3$ | H | H | 1 | $COOCH_3$ | 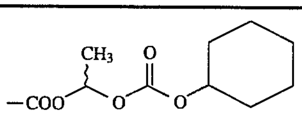 | 1.25–2.00(10H, m), 1.65(3H, s), 2.80–3.05(4H, m), 3.55–5.05(11H, m), 3.60 (3H, s), 3.75(3H, s), 5.10(2H, s), 6.73–7.55(4H, m), 7.35(5H, m) |

TABLE 8-continued

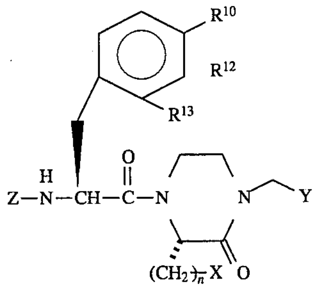

| R. Ex. No. | $R^{10}$ | $R^{12}$ | $R^{13}$ | n | X | Y | $H^1$-NMR ($CDCl_3$: δ) |
|---|---|---|---|---|---|---|---|
| 42 | $OCH_3$ | H | H | 1 | $COOCH_3$ | 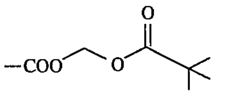 | 1.22(9H, s), 2.30–4.20(10H, m), 3.63 (3H, s), 3.78(3H, s), 4.81(1H, m), 4.97 (1H, m), 5.10(2H, s), 5.55(1H, d, J=9Hz) 5.77(2H, s), 6.82(2H, d, J=9Hz), 7.10 (2H, d, J=9Hz), 7.35(5H, brs) |
| 43 | $OCH_3$ | H | H | 1 | $COOCH_3$ | 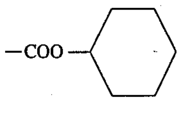 | 1.20–1.95(10H, m), 2.80–3.05(4H, m) 3.50–4-10(7H, m), 3.63(3H, s), 3.78 (3H, s), 4.70–4.88(1H, m), 4.91–5.05 (1H, m), 5.13 (2H, s), 5.57 (1H, d, J=9Hz) 6.82(2H, d J=8Hz), 7.15(2H, d J=8Hz), 7.35(5H, brs) |

EXAMPLE 32

(S)-4-(4-Amidinobenzoyl-O-Methyl-L-Tyrosyl)-3-Methoxycarbonylmethyl-2-Oxopiperazine-1-Acetic Acid Dimethylaminocarbonylmethyl Ester Hydrochloride In 15.0 ml of methanol was dissolved 1.50 g of (S)-4-(N-benzyloxycarbonyl-O-methyl-L-tyrosyl)-3-methoxycarbonylmethyl-2-oxopiperazine-1-acetic acid dimethyl aminocarbonylmethyl ester. To the solution was added 6.0 g of 10% palladium-carbon. The mixture was stirred for 1.5 hour at room temperature under hydrogen atmosphere. The catalyst was filtered off, and the filtrate was concentrated under reduced pressure. This product was dissolved in a mixture solvent of 11.4 ml of water and 5.7 ml of 1.4-dioxane. To the solution was added 0.29 g of sodium hydrogencarbonate and 0.38 g of 4-amidinobenzoyl chloride hydrochloride at room temperature over 5 minutes. The mixture was stirred for one hour, which was then adjusted to pH range of 2 to 3, followed by concentration under reduced pressure. The residue was purified by means of a CHP-20 column ($H_2O$→5% $CH_3CN/H_2O$→10% $CH_3CN/H_2O$→15%) and an LH-20 column ($H_2O$) to afford 0.43 g (50.8%) of the title compound as a white lyophilized product.

Specific rotation $[\alpha]_D^{20}$+73.10° (C=0.71, $H_2O$)

Elemental Analysis: $C_{31}H_{39}N_6O_9Cl.3.0H_2O$ (729,183)

Calcd.: C, 51.06; H, 6.22; N, 11.53

Found: C, 51.15; H, 5.94; N, 11.54

Compounds of Reference Example No. 41, 42 and 43 were subjected to substantially the same procedure as Example 32 to afford compounds of Example Nos. 33 to 35.

TABLE 9

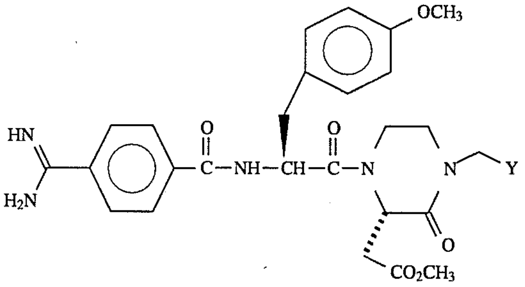

| W. Ex. No. | Y | mp (°C.) | Specific rotation $[a]_D^{20}$ | Rational Formula | Elemental Analysis Calcd. (Found) C | H | N |
|---|---|---|---|---|---|---|---|
| 33 | 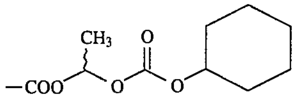 | Powder | +57.9° (C = 0.4, $H_2O$) | $C_{36}H_{45}N_5O_{11}$ $HCl.2H_2O$ | 54.30 (54.35) | 6.33 (6.12) | 8.80 (8.88) |
| 34 | 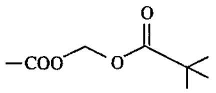 | Powder | +51.6° (C = 0.65, MeOH) | $C_{33}H_{41}N_5O_{10}$ $.HCl.H_2O$ | 54.88 (55.06) | 6.14 (6.07) | 9.70 (9.76) |
| 35 | 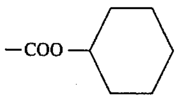 | Powder | +72.9° (C = 0.25, $H_2O$) | $C_{33}H_{41}N_5O_8$ $.HCl.2.5H_2O$ | 55.26 (55.26) | 6.61 (6.21) | 9.76 (9.51) |

EXAMPLE 36

(S)-4-{4-(2-Aminoethyl)Benzoyl-O-Methyl-L-Tyrosyl}-3-Methoxycarbonylmethyl-2-Oxopiperazine-1-Acetic Acid Dimethylaminocarbonylmethyl Ester Hydrochloride In 15.0 ml of methanol was dissolved 1.50 g of (S)-4-(N-benzyloxycarbonyl-O-methyl-L-tyrosyl)-3-me-thoxy-carbonylmethyl-2-oxopiperazine-1-acetic acid dimethy-laminocarbonylmethyl ester obtained in Reference Example 40. To the solution was added 6.0 g of 10% palladium-carbon. The mixture was stirred for 1.5 hour at room temperature under hydrogen atmosphere. The catalyst was filtered off, and the filtrate was concentrated under reduced pressure. In 5.7 ml of methylene chloride were dissolved 570 mg of the residue and 0.42 mg of 4-(2-benzyloxycar-bonylaminoethyl)benzoic acid. To the solution was added, while cooling with water, 0.29 g of 1-(3-dimethylaminopro-pyl)-3-ethylcarbodiimide hydrochloride, over 5 minutes. The mixture was stirred for 2 hours, which was then concentrated under reduced pressure. The residue was dis-solved in ethyl acetate, followed by washing with a 5% aqueous solution of potassium hydrogensulfate and a saturated aqueous solution of sodium hydrogencarbonate. The organic layer was concentrated under reduced pressure. The concentrate was roughly purified by means of a silica gel chromatography (methylene chloride/methanol=13/1). This crude product was dissolved in a mixture of 6.0 ml of methanol and 853 μl of 1N HCl. To the solution was added 180 mg of 10% palladium-carbon, and the mixture was stirred for 40 minutes at room temperature under hydrogen atmosphere. The catalyst was filtered off, and the filtrate was concentrated under reduced pressure. The residue was purified by means of a CHP-20 column ($H_2O$→5% $CH_3CN/H_2O$ →10% $CH_3CN/H_2O$→15% $CH_3CN/H_2O$) to afford 0.39 g (69.6%) of the title compound as a white lyophilized product.

Specific rotation $[E]_D^{20}$+73.8° (C=0.74, $H_2O$)

Elemental Analysis: $C_{32}H_{42}N_5O_9Cl.2.5H_2O$ (729,2029)

Calcd.: C, 53.29; H, 6.57; N, 9.71

Found: C, 53.27; H, 6.35; N, 9.81

Compounds of Reference Example Nos. 41, 42 and 43 were subjected to substantially the same procedure as in Example 36 to give compounds of Example Nos. 37 to 39.

TABLE 10

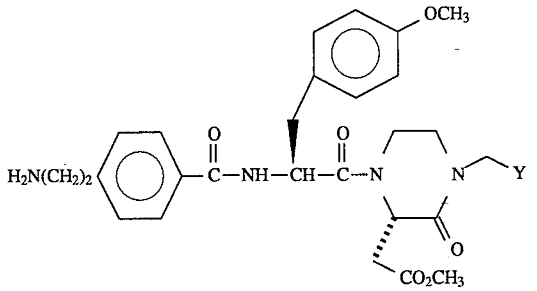

| W. Ex. No. | Y | mp (°C.) | Specific rotation $[a]_D^{20}$ | Rational Formula | Elemental Analysis Calcd. (Found) C | H | N |
|---|---|---|---|---|---|---|---|
| 37 | 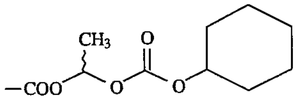 | Powder | +55.4° (C = 0.35, MeOH) | $C_{37}H_{48}N_4O_{11}$ .HCl.2$H_2O$ | 55.74 (55.50) | 6.70 (6.60) | 7.03 (7.17) |
| 38 | 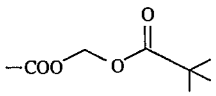 | Powder | +55.0° (C = 0.67, MeOH) | $C_{34}H_{44}N_4O_{10}$ .HCl.$H_2O$ | 56.47 (56.36) | 6.55 (6.48) | 7.75 (7.71) |
| 39 | 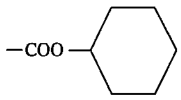 | Powder | +59.3° (C = 0.45, MeOH) | $C_{34}H_{44}N_4O_8$ .HCl.$H_2O$ | 59.08 (58.83) | 6.85 (7.19) | 8.11 (8.13) |

REFERENCE EXAMPLE 44

(S)-4-(N-Tert-Butoxycarbonyl-O-Methyl-L-Tyrosyl)-3-Methoxycarbonylmethyl-2-Oxopiperazine-1-Acetic Acid In 300 ml of methanol was dissolved 19 g of (S)-4-(N-benzyloxycarbonyl-O-methyl-L-tyrosyl)-3-methoxycarbonylmethyl-2-oxopiperazine-1-acetic acid. To the solution was added 2.5 g of 10% palladium-carbon, and the mixture was stirred under hydrogen atomosphere for 1.5 hour. The catalyst was filtered off, and the filtrate was concentrated under reduced pressure. The residue was dissolved in a mixture of 200 ml of water and 50 ml of 1,4-dioxane, to which was added 7.36 ml of triethylamine. To the mixture was added, under ice-cooling, 8.4 g of di-t-butyl dicarbonate. The reaction mixture was adjusted to pH 2 with 5% potassium hydrogensulfate, followed by extraction with ethyl acetate and drying over anhydrous sodium sulfate. The extract solution was concentrated under reduced pressure to give 16.5 g of the title compound in a crude state as a colorless powdery product.

IRvmax $cm^{-1}$: 3400, 2975, 1735, 1710, 1665, 1510, 1440, 1365, 1300, 1245, 1210, 1170, 1030

NMR($CDCl_3$)δ: 1.42(s,9H), 2.30–4.20(m,10H), 3.64(s,3H), 3.76(s,3H), 4.76(m,1H), 4.99(t,J=5.2 Hz,1H), 5.12(d,J=8.4 Hz,1H), 6.82(d,J=8.4 Hz,2H), 7.09(d,J=8.4 Hz,2H)

REFERENCE EXAMPLE 45

(S)-4-(N-$^t$Butoxycarbonyl-O-Methyl-L-Tyrosyl)-3-Methoxycarbonylmethyl-2-Oxopiperazine-1-Acetic Acid (3-Phthalidylidene) Ethyl Ester In 8.66 ml of N-dimethylformamide were dissolved 2.2 g of (S)-4-(N-$^t$butoxycarbonyl-O-methyl-L-tyrosyl)3-methoxycarbonylmethyl-2-oxopiperazine-1-acetic acid and 1.52 g of potassium hydrogencarbonate. To the solution was added 1.55 g of (Z)-3-(2-bromoethylidene) phthalide while stirring at 0° C. The mixture was stirred for 2 hours at room temperature, to which was added water, followed by shaking with ethyl acetate for extraction. The organic layer was concentrated under reduced pressure. The residue was purified by means of a silica gel chromatography (methylene chloride/ethyl acetate=6/3.5) to give 1.82 g of the title compound (63.2%) as a colorless oily product.

IRvmax $cm^{-1}$: 2976, 2948, 1786, 1740, 1705, 1650, 1512, 1438, 1363, 1246, 1177, 978, 819, 764, 690, 635

NMR($CDCl_3$)δ: 1.43(s,9H), 2.37–2.58(m, 1H), 2.76–3.30(m,5H), 3.50–3.90(m,2H), 3.65(s,3H), 3.78(s,3H), 4.09(dd,J=17.0 Hz,J=24.6 Hz,2H), 4.64–4.82(m,1H), 4.92–5.11(m,3H), 5.36(d,J=8.0 Hz,1H), 5.75(t,J=7.4 Hz,1H), 6.83(d,J=8.4 Hz,2H), 7.03–7.26(m,2H), 7.53–7.83(m,3H), 7.92(d,J=8.2 Hz,1H)

By substantially the same procedure as in Reference Example 45, compounds of Reference Example Nos. 46 and 47 were obtained as colorless oily product.

TABLE 11

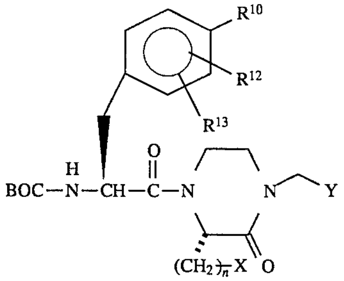

| R. Ex. No. | $R^{10}$ | $R^{12}$ | $R^{13}$ | n | X | Y | $H^1$-NMR ($CDCl_3$: δ) |
|---|---|---|---|---|---|---|---|
| 46 | $OCH_3$ | H | H | 1 | $COOCH_3$ | 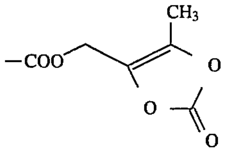 | 1.42(9H, s), 2.17(3H, s), 2.88–3.06 (4H, m), 3.60–3.90(6H, m), 3.65(3H, s) 3.77(3H, s), 4.65–4.81(1H, m), 4.88 (2H, s), 4.95(1H, m), 5.25–5.33(1H, m) 6.80(2H, d J=8Hz), 7.10(2H, d J=8Hz) |
| 47 | $OCH_3$ | H | H | 1 | $COOCH_3$ | 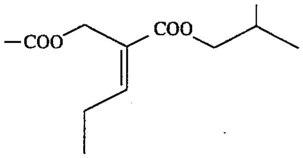 | 0.95 (6H, d J=6.6Hz), 1.08 (3H, t J=7.6 Hz), 1.34(9H, s), 1.98(1H, m), 2.32(2H, m), 2.30–4.10(10H, m), 3.65(3H, s), 3.77(3H, s), 3.95(2H, d J=6.6Hz), 4.60–5.10(4H, m), 5.27(1H, m), 6.75–7.20 (5H, m) |

EXAMPLE 40

(S)-4-(4-Amidinobenzoyl-O-Methyl-L-Tyrosyl)-3-Methoxycarbonylmethyl-2-Oxopiperazine-1-Acetic Acid (3Phthalidylidene)Ethyl Ester Hydrochloride In a mixture of 5.1 ml of methylene chloride and 5.1 ml of trifluoroacetic acid was dissolved 1.71 g of (S)-4-(N-'butoxycarbonyl-O-methyl-L-tyrosyl)-3-methoxycarbonylmethyl-2-oxopiperazine-1-acetic acid (3phthalidylidene) ethyl ester. The solution was stirred for 1.0 hours at room temperature. The reaction solution was concentrated under reduced pressure. The residue was subjected to azeotropy several times with toluene. In a mixture solvent of 17.0 ml of $H_2O$ and 8.5 ml of 1,4-dioxane was dissolved 850 mg of the product. To the solution was added at room temperature 0.53 g of sodium hydrogencarbonate, to which was added 0.41 g of 4-amidinobenzoylchloride hydrochloride at room temperature over 5 minutes. The mixture was stirred for one hour, whose pH was adjusted to pH 2 to 3 with 1N HCl, then the reaction mixture was concentrated under reduced pressure. The concentrate was purified by means of a CHP-20 column ($H_2O$→5% $CH_3CN/H_2O$→10% $CH_3CN/H_2O$→15% $CH_3CN/H_2O$→20% $CH_3CN/H_2O$ →25% $CH_3CN/H_2O$→30% $CH_3CN/H_2O$), an LH-20 column (MeOH) and a silica gel chromatography ($CH_3CN/H_2O$=5/1) to give 0.27 g (26.0%) of the title compound as a white lyophilized product.

Specific rotation $[\alpha]_D^{20}$+51.5° (C=0.77, $H_2O$) p0 Elemental Analysis: $C_{37}H_{37}N_5O_{10}$.0.7HCl.0.3$CF_3CO_2H$.3.5$H_2O$ (834,510)

Calcd.: C, 54,12; H, 5.43; N, 8.39

Found: C, 54.11; H, 5.21; N, 8.64

Compounds of Reference Example Nos. 46 and 47 were subjected to substantially the same procedure as in Example 40 to give compounds of Example Nos. 41 and 42.

TABLE 12

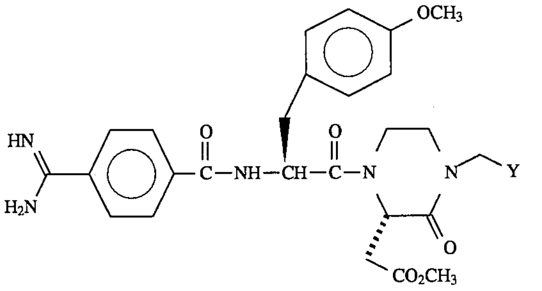

| R. Ex. No. | Y | mp (°C.) | Specific rotation $[a]_D^{20}$ | Rational Formula | Elemental Analysis Calcd. (Found) C | H | N |
|---|---|---|---|---|---|---|---|
| 41 | 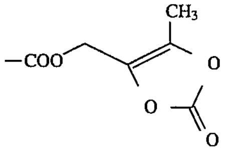 | Powder | +27.5° (C = 0.3, $H_2O$) | $C_{32}H_{35}N_5O_{11}$ .HCl.2$H_2O$ | 52.07 (52.11) | 5.46 (5.26) | 9.49 (9.23) |
| 42 | 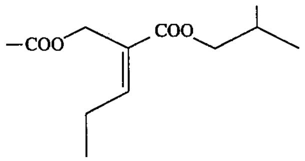 | Powder | +46.9° (C = 0.6, MeOH) | $C_{37}H_{47}N_5O_{10}$ .$CF_3CO_2H$.$H_2O$ | 54.86 (54.87) | 5.90 (5.78) | 8.20 (8.20) |

EXAMPLE 43

(S)-4-{4-(2-Aminoethyl)Benzoyl-O-Methyl-L-Tyrosyl)-3-Methoxycarbonylmethyl-2-Oxopiperazine-1-Acetic Acid (3Phthalidylidene)Ethyl Ester Hydrochloride In a mixture of 5.1 ml of methylene chloride and 5.1 ml of trifluoroacetic acid was dissolved 1.71 g of (S)-4-(N-$^t$butoxycarbonyl-O-methyl-L-tyrosyl)-3-methoxycarbonylmethyl-2-oxopiperazine-1-acetic acid (3-phthalidylidene-)ethyl ester. The solution was stirred for 1.0 hours at room temperature. The reaction solution was concentrated under reduced pressure, which was subjected to azeotropy several times with toluene. This product (860 mg) was dissolved in a mixture of 4.3 ml of methylene chloride and 531 μl of triethylamine, which was added to a solution of 0.2 g of 1-hydroxybenztriazole, 0.37 g of 4-(2-$^t$butoxycarbonylaminoethyl) benzoic acid and 0.28 g of 1(3-dimetylaminopropyl)-3-ethylcarbodiimide. The mixture was stirred for one hour, and the reaction solution was concentrated under reduced pressure. The residue was dissolved in ethyl acetate, which was washed with 5% potassium hydrogensulfate and a saturated aqueous solution of sodium hydrogencarbonate. The organic layer was concentrated under reduced pressure. The concentrate was roughly purified by means of a silica gel chromatography (methylene chloride/ethyl acetate=1/4). This product was dissolved in a mixture of 2.46 ml of methylene chloride and 2.64 ml of trifluoroacetic acid. The reaction solution was concentrated under reduced pressure, which was subjected to azeotropy several times with toluene, which was then converted into hydrochloride with 1N HCl. The residue was purified by means of a CHP-20 column ($H_2O$→5% $CH_3CN/H_2O$→10% $CH_3CN/H_2O$→15% $CH_3CN/H_2O$→20% $CH_3CN/H_2O$→25% $CH_3CN/H_2O$→30% $CH_3CN/H_2O$), an LH-20 column (MeOH to afford 0.22 g (24.7 %) of the title compound as a white lyophilized product.

Specific rotation $[\alpha]_D^{20}$+49.3° (C=0.31, $H_2O$)

Elemental Analysis: $C_{38}H_{40}N_4O_{10}$.0.7HCl.0.3$CF_3CO_2H$.2.0$H_2O$ (808,515)

Calcd.: C, 57.34; H, 5.61; N, 6.93

Found: C, 57.02; H, 5.35; N, 6.81

Compounds of Reference Example 46 and 47 were subjected to substantially the same procedure as in Example 43 to give compounds 44 and 45.

TABLE 13

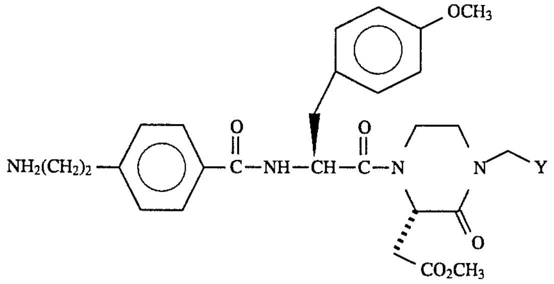

| W. Ex. No. | Y | mp (°C.) | Specific rotation $[a]_D^{20}$ | Rational Formula | Elemental Analysis Calcd. (Found) C | H | N |
|---|---|---|---|---|---|---|---|
| 44 | 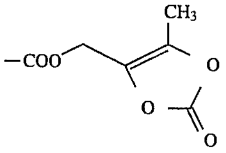 | Powder | +59.3° (C = 0.74, MeOH) | $C_{33}H_{38}N_4O_{11}$ .HCl.2$H_2O$ | 53.62 (53.35) | 5.86 (5.48) | 7.58 (7.58) |
| 45 | 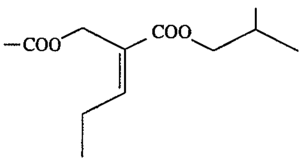 | Powder | +50.6° (C = 0.6, MeOH) | $C_{38}H_{50}N_4O_{10}$ .1/2HCl.1/2 $CF_3CO_2H$.1/2$H_2O$ | 58.04 (58.17) | 6.49 (6.38) | 6.94 (7.27) |

Examples of Formulation

In the case of using the compound (I) of this invention as a therapeutic agent of, for example, thrombosis, use is made of, for example, the following prescriptions.

| | | |
|---|---|---|
| (1) | (S)-4-(4-amidinobenzoyl-L-tyrosyl)-3-methoxy-carbonylmethyl-2-oxopiperazine-l-acetic acid | 10 g |
| (2) | lactose | 90 g |
| (3) | corn starch | 29 g |
| (4) | magnesium stearate | 1 g |
| | | 130 g |

The whole amounts of (1) and (2) are mixed with 17 g of (3) and the mixture is granulated with a paste prepared from 7 g of (3). With the granules mixed 5 g of (3) and the whole amount of (4). The whole mixture is subjected to compression molding on as compression tableting machine to give 1000 tablets 7 mm in diameter and each containing 10 mg of (1). 2. Injections

| | | |
|---|---|---|
| (1) | (S)-4-(4-amidinobenzoyl-L-tyrosyl)-3-methoxy-carbonylmethyl-2-oxopiperazine-l-acetic acid | 10 g |
| (2) | sodium chloride | 9 g |

The whole amounts of (1) and (2) are dissolved in 1000 ml of distilled water. One ml each of the solution is put in 1000 brown ampoules. Air in the ampoules is replaced with nitrogen gas, and the ampoules are sealed. The whole procedure is conducted under sterilized conditions. 3. Tablets

| | | |
|---|---|---|
| (1) | (S)-4-(4-amidinobenzoyl-O-methyl-L-tyrosyl)-3-methoxy-carbonylmethyl-2-oxopiperazine-1-acetic acid | 10 g |
| (2) | lactose | 90 g |
| (3) | corn starch | 29 g |
| (4) | magnesium stearate | 1 g |
| | | 130 g |

The whole amounts of (1) and (2) are mixed with 17 g of (3) and the mixture is granulated with a paste prepared from 7 g of (3). With the granules mixed 5 g of (3) and the whole amount of (4). The whole mixture is subjected to compression molding on as compression tableting machine to give 1000 tablets 7 mm in diameter and each containing 10 mg of (1). 4. Injections

| | | |
|---|---|---|
| (1) | (S)-4-(4-amidinobenzoyl-O-methyl-L-tyrosyl)-3-methoxy-carbonylmethyl-2-oxopiperazine-1-acetic acid | 10 g |
| (2) | sodium chloride | 9 g |

The whole amounts of (1) and (2) are dissolved in 1000 ml of distilled water. One ml each of the solution is put in 1000 brown ampoules. Air in the ampoules is replaced with nitrogen gas, and the ampoules are sealed. The whole procedure is conducted under sterilized conditions.

We claim:

1. A compound of the formula

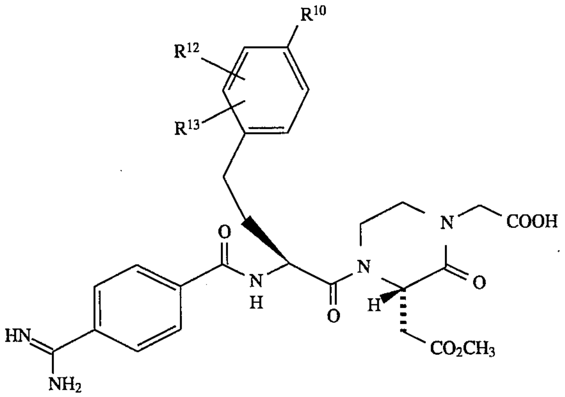

wherein $R^{10}$ is OH, $OCH_3$, $O(CH_2)_2$ $CH_3$, $OCH_2O$ $(CH_2)$ $OCH_3$, $OCH_2CH{=}CH_2$, $OCH_2$ $C{\equiv}CH$, or F, $R^{12}$ is H, F or OH, and $R^{13}$ is H or F; or a pharmaceutically salt thereof.

2. A compound according to claim 1, which is (S)-4-(4-amidinobenzoyl-O-methyl-L-tyrosyl)-3-methoxycarbonylmethyl-2-oxopiperazine-1-acetic acid or its salt.

3. (S)-4-{4-(2-Aminoethyl)benzoyl-O-methyl-L-tyrosyl}-3-methoxycarbonyl-2-oxopiperazine-1-acetic acid or its salt.

4. A composition for preventing or treating obstruction or re-obstruction caused by cell-adhesion, which comprises a compound claimed in claim 1, a pharmaceutically acceptable salt thereof.

5. A composition for preventing or treating thrombosis, which comprises a compound claimed in claim 1 or a pharmaceutically acceptable salt thereof.

6. A method for preventing or treating obstruction or reobstruction caused by cell-adhesion, which comprises administering an effective amount of a compound as claimed in claim 1 or a pharmaceutically acceptable salt thereof and a pharmaceutically acceptable excipient to a mammal.

7. A method for preventing or treating thrombosis, which comprises administering an effective amount of a compound as claimed in claim 1 or a pharmaceutically acceptable salt thereof and a pharmaceutically acceptable excipient to a mammal.

* * * * *

UNITED STATES PATENT AND TRADEMARK OFFICE

CERTIFICATE OF CORRECTION

PATENT NO. : 5,550,131

DATED : August 27, 1996

INVENTOR(S) : Hirosada SUGIHARA et al.

It is certified that error appears in the above-indentified patent and that said Letters Patent is hereby corrected as shown below:

Column 9, line 30, contains a typographical error wherein "$CH_2)_{\underline{2}}$-X" should read --$(CH_2)_{\underline{n}}$-X--; line 35, "$(CH_2)_{\underline{2}}$-X" should read --$(CH_2)_{\underline{n}}$-X--.

Columns 25 and 26, Table 7, "$OR^{11}$" should read --$R^{10}$--.

Columns 41 and 42, Table 10, "$H_2N(CH_2)_2$" should read --$H_2N(CH_2)_2\equiv$ --.

Claim 1, line 44, column 49, "$OCH_2C = CH$" should read --OCH2C $\equiv$ CH--.

Claim 4, line 31, column 50, before "a" insert --or--.

Signed and Sealed this

Thirteenth Day of May, 1997

Attest:

BRUCE LEHMAN

*Attesting Officer* *Commissioner of Patents and Trademarks*